US012191031B2

(12) United States Patent
Azizian et al.

(10) Patent No.: US 12,191,031 B2
(45) Date of Patent: Jan. 7, 2025

(54) BEACON-BASED SYSTEMS AND METHODS FOR MANAGING ACCESS TO APPLICATION FEATURES ASSOCIATED WITH A MEDICAL SESSION

(71) Applicant: Intuitive Surgical Operations, Inc., Sunnyvale, CA (US)

(72) Inventors: Mahdi Azizian, San Jose, CA (US); Christopher R. Burns, San Jose, CA (US); Boris Foelsch, Palo Alto, CA (US); Liron Leist, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 885 days.

(21) Appl. No.: 17/103,686

(22) Filed: Nov. 24, 2020

(65) Prior Publication Data

US 2021/0158955 A1    May 27, 2021

Related U.S. Application Data

(60) Provisional application No. 62/940,797, filed on Nov. 26, 2019.

(51) Int. Cl.
*G16H 40/60* (2018.01)
*A61B 1/00* (2006.01)
*G16H 10/60* (2018.01)
*G16H 40/63* (2018.01)

(52) U.S. Cl.
CPC ........... *G16H 40/63* (2018.01); *A61B 1/0004* (2022.02); *A61B 1/00042* (2022.02); *G16H 10/60* (2018.01); *G16H 40/60* (2018.01); *A61B 1/00009* (2013.01)

(58) Field of Classification Search
CPC ......... G16H 40/20; G16H 80/00; G16H 15/00
See application file for complete search history.

(56) References Cited

U.S. PATENT DOCUMENTS

2019/0378610 A1* 12/2019 Barral .................... G09B 19/24
2023/0215530 A1*  7/2023 McNair .................. G06Q 50/22
                                                              235/375

FOREIGN PATENT DOCUMENTS

WO    WO-2021091437 A1 *  5/2021  ............. G06F 21/32

OTHER PUBLICATIONS

Wilikens, Marc, et al. "A context-related authorization and access control method based on rbac." Proceedings of the seventh ACM symposium on Access control models and technologies. 2002. (Year: 2002).*
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

*Primary Examiner* — Jason B Dunham
*Assistant Examiner* — Constantine Siozopoulos

(57) ABSTRACT

An application management system may provide, while a user device detects a beacon associated with a medical system, a user of the user device with access to a first set of medical session features of an application executed by the user device. The application management system may also provide, while the user device does not detect the beacon, the user with access to a second set of medical session features of the application, the second set of medical session features being different from the first set of medical session features.

20 Claims, 16 Drawing Sheets

BEACON-BASED SYSTEMS AND METHODS FOR MANAGING ACCESS TO APPLICATION FEATURES ASSOCIATED WITH A MEDICAL SESSION

RELATED APPLICATIONS

The present application claims priority to U.S. Provisional Patent Application No. 62/940,797, filed on Nov. 26, 2019, and entitled "BEACON-BASED SYSTEMS AND METHODS FOR MANAGING ACCESS TO APPLICATION FEATURES ASSOCIATED WITH A MEDICAL SESSION," the contents of which are hereby incorporated by reference in their entirety.

BACKGROUND INFORMATION

In a medical facility (e.g., a hospital, a nursing home, etc.), medical personnel may use a medical system to diagnose, treat, and/or assist patients. In some medical facilities the medical personnel may also use a user device (e.g., a tablet computer, a smartphone, etc.) in the diagnosis, treatment, and/or assistance of the patient. For example, during a computer-assisted surgical procedure, such as a minimally invasive surgical procedure performed at a surgical facility, a surgeon may interact with a computer-assisted surgical system to control teleoperated surgical instruments to perform the surgical procedure on a patient. Other surgical team members may also interact with the computer-assisted surgical system to assist with the surgical procedure. A surgical team member (e.g., a nurse) may also use a user device (e.g., a mobile phone, a tablet computer, etc.) during the surgical procedure, such as to view information about the patient or the computer-assisted surgical system.

SUMMARY

The following description presents a simplified summary of one or more aspects of the methods and systems described herein in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects of the methods and systems described herein in a simplified form as a prelude to the more detailed description that is presented below.

An exemplary system may comprise a memory storing instructions and a processor communicatively coupled to the memory and configured to execute the instructions to provide, while a user device detects a beacon associated with a medical system, a user of the user device with access to a first set of medical session features of an application executed by the user device, and provide, while the user device does not detect the beacon, the user with access to a second set of medical session features of the application, the second set of medical session features being different from the first set of medical session features.

An exemplary method may comprise providing, by an application management system while a user device detects a beacon associated with a medical system, a user of the user device with access to a first set of medical session features of an application executed by the user device and providing, by the application management system while the user device does not detect the beacon, the user with access to a second set of medical session features of the application, the second set of medical session features being different from the first set of medical session features.

An exemplary non-transitory computer-readable medium stores instructions that, when executed, direct at least one processor of a computing device to provide, while a user device detects a beacon associated with a medical system, a user of the user device with access to a first set of medical session features of an application executed by the user device and provide, while the user device does not detect the beacon, the user with access to a second set of medical session features of the application, the second set of medical session features being different from the first set of medical session features.

An exemplary user device may comprise a memory storing instructions and a processor communicatively coupled to the memory and configured to execute the instructions to provide, while the user device detects a beacon associated with a medical system, a user of the user device with access to a first set of medical session features and provide, while the user device does not detect the beacon, the user with access to a second set of medical session features, the second set of medical session features being different from the first set of medical session features.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
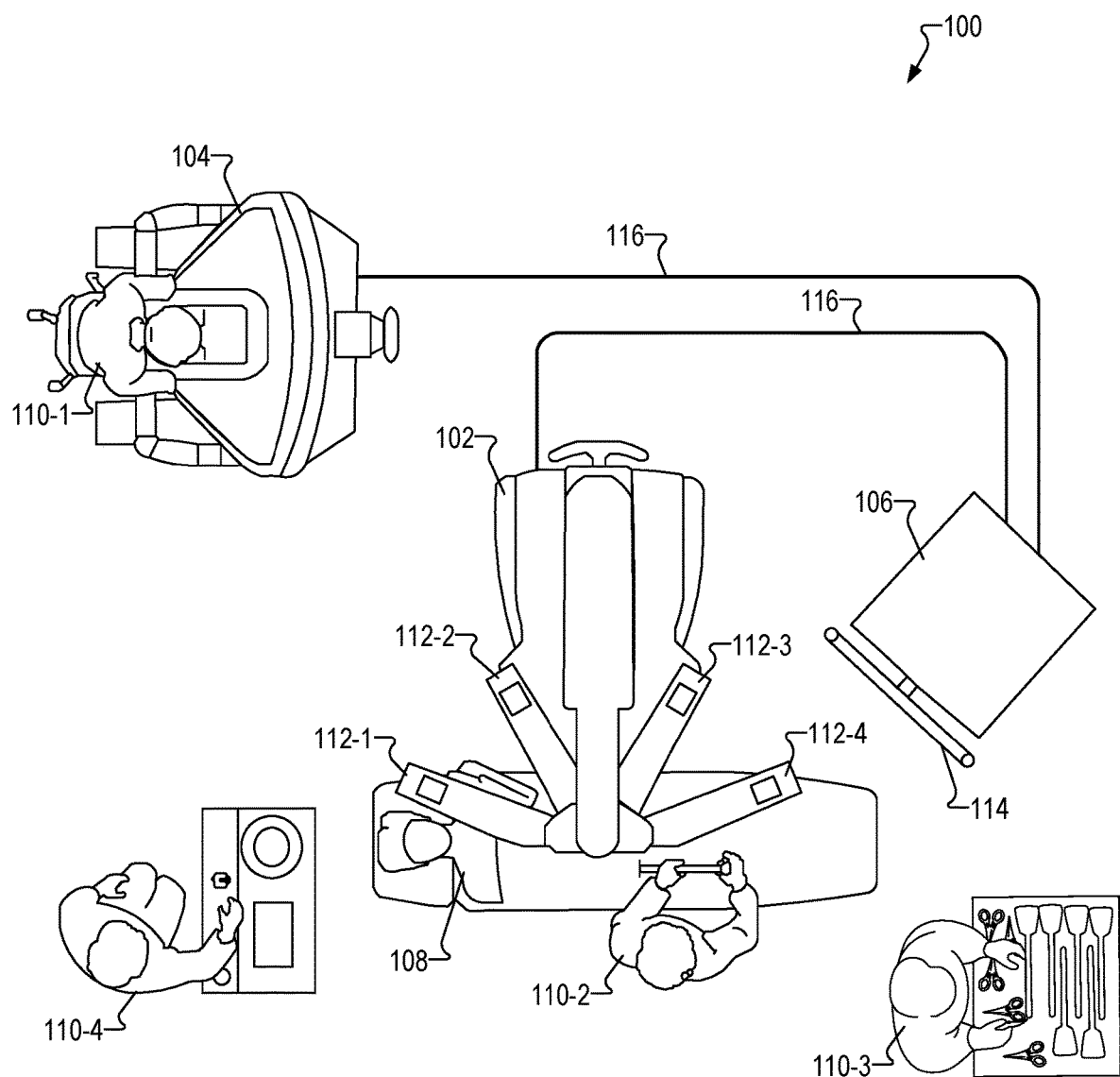
FIG. 1 illustrates an exemplary computer-assisted surgical system according to principles described herein

Beacon-based systems and methods for managing access to application features associated with a medical session are described herein. As will be described below in more detail, a beacon-based application management system may provide, while a user device detects a beacon associated with a medical system, a user of the user device with access to a first set of medical session features of an application executed by the user device. While the user device does not detect the beacon, the beacon-based application management system may provide the user with access to a second set of medical session features of the application, the second set of medical session features being different from the first set of medical session features.

In some examples, the first set of medical session features and the second set of medical session features are associated with the same medical session associated with the medical system (e.g., a medical session performed with the medical system and/or in the same predefined area in which the medical system is located). As used herein, a medical session may refer to a set of one or more procedures, activities, and/or tasks that may be performed with respect to a patient to diagnose, measure, monitor, treat, and/or assist the patient. A medical session may include, for example, a surgical procedure (including preoperative, operative, and postoperative phases) and/or a non-surgical procedure. Surgical and non-surgical procedures may include propaedeutic procedures (e.g., a physical examination, a physician consultation, etc.), diagnostic procedures (e.g., an x-ray scan, an angiogram, a magnetic resonance imaging (MRI) scan, a computed tomography (CT) scan, an ultrasound scan, an electrocardiography (ECG) scan, an electroencephalography (EEG) scan, a biopsy, a blood test, an endoscopy, a colonoscopy, etc.), therapeutic procedures (e.g., administration of medication, a radiation treatment, a surgical operation, etc.), rehabilitative procedures (e.g., physical therapy procedures, speech pathology procedures, etc.), and/or any other suitable procedure.

Medical session features associated with a medical session and provided by way of an application executed by a user device allow the user to interact with the user device to perform various operations and tasks associated with the medical session, such as view content associated with the medical session, provide information associated with the medical session, interact with a medical system associated with the medical session (e.g., a computer-assisted surgical system), and/or communicate with other personnel (e.g., medical personnel, the patient, the patient's family, etc.) associated with the medical session.

To illustrate, a surgeon carrying a mobile device (e.g., a tablet computer) may enter an operating room in which a computer-assisted surgical system will be used to perform a surgical procedure on a patient. When the surgeon enters the operating room, the mobile device may detect an ultrasonic beacon emitted by a beacon generator in the operating room. In response and while the mobile device detects the ultrasonic beacon, the beacon-based application management system may automatically provide the surgeon with access, by way of an application executed by the mobile device, to view and interact with pre-operative medical images associated with the patient (e.g., MRI images, CT images, 3D models, etc.). After the surgical procedure concludes and while the mobile device does not detect the ultrasonic beacon, the beacon-based application management system may provide the surgeon with access to play back a recording of an endoscopic video feed of the surgical procedure.

In some examples the beacon-based application management system may provide access to the application features based on one or more other factors, such as information included in the beacon (e.g., information identifying a particular a predefined area of the medical facility, information identifying the medical session, and/or information identifying a medical system associated with the medical session), user data (e.g., an identity of the user of the user device, a user role of the user (e.g., surgeon, nurse, assistant, etc.), and/or a user profile of the user), proximity of the user device to the beacon generator and/or a medical system component, and/or any suitable other factor.

For instance, the beacon-based application management system may identify, in response to a determination that a user device detects an ultrasonic beacon, a particular surgical session identifier included in the ultrasonic beacon. The beacon-based application management system may then provide a user of the user device with access to a particular set of features associated with the particular surgical session (e.g., access to patient records for the patient of the surgical session, surgical team information, surgical procedure information, etc.).

As another example, in response to the determination that the user device detects the ultrasonic beacon, the beacon-based application management system may access (e.g., from the user device) user data and determine, based on the user data, that the user of the user device is authorized to access a particular set of medical session features of the application (e.g., patient record editing features, medical system interaction features, etc.). Based on the determination that the user is authorized to access the particular set of medical session features of the application, the beacon-based application management system may provide the user with access to the particular set of medical session features of the application.

In certain examples the beacon-based application management system may also dynamically change the set of features provided by way of the user device in response to various situational changes during a medical session. For example, the beacon-based application management system may terminate the access to the first set of medical session features and/or provide the user with access to a different set of medical session features in response to a determination that the user device no longer detects the ultrasonic beacon, the user device detects another ultrasonic beacon, the ultrasonic beacon is updated to include new information, the user data associated with the user device changes, and/or any other situational change.

The systems and methods described herein may provide various benefits. For example, the systems and methods described herein may automatically provide a user with access, by way of a user device, to different sets of application features associated with a medical session based on physical proximity of the user device to a location where the medical session will occur, is occurring, or has occurred. Additionally, the systems and methods described herein automatically select the set of application features based on the particular details of the medical session and/or the user of the user device. Thus, the systems and methods described herein automatically provide the user with access to only those application features that are useful and relevant to the user. As a result, use and operation of the application during a medical session is intuitive and efficient for the user. These and other benefits of the systems and methods described herein will be made apparent in the description that follows.

The beacon-based application management systems and methods described herein may be implemented as part of or in conjunction with a medical system, such as a computer-assisted surgical system. As such, an exemplary computer-assisted surgical system will now be described. The following exemplary computer-assisted surgical system is illustrative and not limiting, as the beacon-based application management systems and methods described herein may be implemented as part of or in conjunction with other suitable medical systems.

FIG. 1 illustrates an exemplary computer-assisted surgical system 100 ("surgical system 100"). As shown, surgical system 100 may include a manipulating system 102, a user control system 104, and an auxiliary system 106 communicatively coupled one to another. In some examples, surgical system 100 may be implemented by one or more of these components. However, surgical system 100 is not limited to these components, and may include additional components as may suit a particular implementation, such as but not limited to a patient operating table, third-party components (e.g., electrosurgical units) connected to surgical system 100, and/or any other component.

Surgical system 100 may be utilized by a surgical team to perform a computer-assisted surgical procedure on a patient 108. As shown, the surgical team may include a surgeon 110-1, an assistant 110-2, a nurse 110-3, and an anesthesiologist 110-4, all of whom may be collectively referred to as "surgical team members 110." Additional or alternative surgical team members may be present during a surgical session as may serve a particular implementation.

While FIG. 1 illustrates an ongoing minimally invasive surgical procedure, surgical system 100 may similarly be used to perform open surgical procedures or other types of surgical procedures that may similarly benefit from the accuracy and convenience of surgical system 100. Additionally, it will be understood that the surgical session throughout which surgical system 100 may be employed may not only include an operative phase of a surgical procedure, as is illustrated in FIG. 1, but may also include preoperative, postoperative, and/or other suitable phases of the surgical procedure. A surgical procedure may include any procedure in which manual and/or instrumental techniques are used on a patient to investigate, diagnose, and/or treat a physical condition of the patient. Additionally, a surgical procedure may include any non-clinical procedure, e.g., a procedure that is not performed on a live patient, such as a calibration or testing procedure, a training procedure, and an experimental or research procedure.

As shown in FIG. 1, manipulating system 102 may include a plurality of manipulator arms 112 (e.g., manipulator arm 112-1 through 112-4) to which a plurality of surgical instruments (not shown in FIG. 1) may be coupled. Each surgical instrument may be implemented by any suitable therapeutic instrument (e.g., a tool having tissue-interaction functions), imaging device (e.g., an endoscope), diagnostic instrument, or the like that may be used for a computer-assisted surgical procedure (e.g., by being at least partially inserted into patient 108 and manipulated to perform a computer-assisted surgical procedure on patient 108). In some examples, one or more of the surgical instruments may include force-sensing and/or other sensing capabilities. While manipulating system 102 is depicted and described herein as including four manipulator arms 112, it will be recognized that manipulating system 102 may include only a single manipulator arm 112 or any other number of manipulator arms as may serve a particular implementation.

Manipulator arms 112 and/or surgical instruments attached to manipulator arms 112 may include one or more sensors (e.g., displacement transducers, orientational sensors, positional sensors, etc.) used to generate (i.e., uncorrected) kinematics information (hereinafter "surgical system sensors"). Kinematics information may include information such as pose (e.g., position and/or orientation), movement (e.g., velocity, direction, acceleration, etc.), state (e.g., open, closed, stowed, etc.), and/or other attributes of manipulator arms 112, surgical instruments coupled to manipulator arms 112, and/or any other components of manipulating system 102 (e.g., boom arms). One or more components of surgical system 100 may be configured to use the kinematics information to track (e.g., determine poses, movements, and/or states of) and/or control manipulator arms 112 and/or surgical instruments. Manipulating system 102 may also include other sensors configured to generate other information as may suit a particular implementation. Such sensors may also be referred to as "surgical system sensors" and may include, for example, draping sensors, boom height sensors, and/or any other sensors.

Surgical instruments attached to manipulator arms 112 may each be positioned at a surgical area associated with a patient. A "surgical area" may, in certain examples, be entirely disposed within a patient and may include an area within the patient at or near where a surgical procedure is planned to be performed, is being performed, or has been performed. For example, for a minimally invasive surgical procedure being performed on tissue internal to a patient, the surgical area may include the tissue, anatomy underlying the tissue, as well as space around the tissue where, for example, surgical instruments being used to perform the surgical procedure are located. In other examples, a surgical area may be at least partially disposed external to the patient at or near where a surgical procedure is planned to be performed, is being performed, or has been performed on the patient. For instance, surgical system 100 may be used to perform an open surgical procedure such that part of the surgical area (e.g., tissue being operated on) is internal to the patient while another part of the surgical area (e.g., a space around the tissue where one or more surgical instruments may be disposed) is external to the patient. A surgical instrument may be referred to as being positioned or located at or within a surgical area when at least a portion of the surgical instrument (e.g., a distal portion of the surgical instrument) is located within the surgical area.

User control system 104 may be configured to facilitate control by surgeon 110-1 of surgical system 100 (e.g., manipulator arms 112 and surgical instruments attached to manipulator arms 112). For example, surgeon 110-1 may interact with user input devices included in user control system 104 to remotely move or manipulate manipulator arms 112 and the surgical instruments coupled to manipulator arms 112. To this end, user control system 104 may provide surgeon 110-1 with imagery (e.g., high-definition stereoscopic imagery) of a surgical area associated with patient 108 as captured by an imaging device (e.g., a stereoscopic endoscope). Surgeon 110-1 may utilize the imagery to perform one or more procedures with one or more surgical instruments coupled to manipulator arms 112.

To facilitate control of surgical instruments, user control system 104 may include a set of master controls (not shown in FIG. 1). These master controls may be manipulated by surgeon 110-1 to control movement of surgical instruments (e.g., by utilizing robotic and/or teleoperation technology). The master controls may be configured to detect a wide variety of hand, wrist, and finger movements by surgeon 110-1. In this manner, surgeon 110-1 may intuitively perform a surgical procedure using one or more surgical instruments.

User control system 104 may further be configured to facilitate control by surgeon 110-1 of other components of surgical system 100. For example, surgeon 110-1 may interact with user control system 104 to change a configuration or operating mode of surgical system 100, to change a display mode of surgical system 100, to generate additional control signals used to control surgical instruments attached to manipulator arms 112, to facilitate switching control from one surgical instrument to another, or to perform any other suitable operation. To this end, user control system 104 may also include one or more additional user input devices (e.g., foot pedals, buttons, switches, touchscreen displays, etc.) configured to receive manual input from surgeon 110-1. In some examples, user control system 104 may also include one or more audio input devices (e.g., microphones) configured to receive audio input (e.g., voice input) from one or more users, and one or more audio output devices (e.g., speakers).

Auxiliary system 106 may include one or more computing devices configured to perform primary processing operations of surgical system 100. The one or more computing devices included in auxiliary system 106 may control and/or coordinate operations performed by various other components (e.g., manipulating system 102 and/or user control system 104) of surgical system 100. For example, a computing device included in user control system 104 may transmit instructions to manipulating system 102 by way of the one or more computing devices included in auxiliary system 106. As another example, auxiliary system 106 may receive, from manipulating system 102 (e.g., from an imaging device), and process image data representative of imagery captured by an endoscope attached to a manipulator arm 112.

In some examples, auxiliary system 106 may be configured to present visual content to surgical team members 110 who may not have access to the imagery provided to surgeon 110-1 at user control system 104. To this end, auxiliary system 106 may include a display monitor 114 configured to display one or more user interfaces, such as images (e.g., 2D images) of the surgical area, information associated with patient 108 and/or the surgical procedure, and/or any other visual content as may serve a particular implementation. For example, display monitor 114 may display images of the surgical area together with additional content (e.g., graphical content, contextual information, etc.) concurrently displayed with the images. In some embodiments, display monitor 114 is implemented by a touchscreen display with which surgical team members 110 may interact (e.g., by way of touch gestures) to provide user input to surgical system 100.

While auxiliary system 106 is shown in FIG. 1 as a separate system from manipulating system 102 and user control system 104, auxiliary system 106 may be included in, or may be distributed across, manipulating system 102 and/or user control system 104. Additionally, while user control system 104 has been described as including one or more user input devices and/or audio input devices, other components of surgical system 100 (e.g., manipulating system 102 and/or auxiliary system 106) may include user input devices, audio input devices, and/or audio output devices as may suit a particular implementation.

Manipulating system 102, user control system 104, and auxiliary system 106 may be communicatively coupled one to another in any suitable manner. For example, as shown in FIG. 1, manipulating system 102, user control system 104, and auxiliary system 106 may be communicatively coupled by way of control lines 116, which may represent any optical, wired, or wireless communication link as may serve a particular implementation. To this end, manipulating system 102, user control system 104, and auxiliary system 106 may each include one or more optical, wired, or wireless communication interfaces, such as one or more local area network interfaces, Wi-Fi network interfaces, cellular interfaces, etc.

Figure 2:
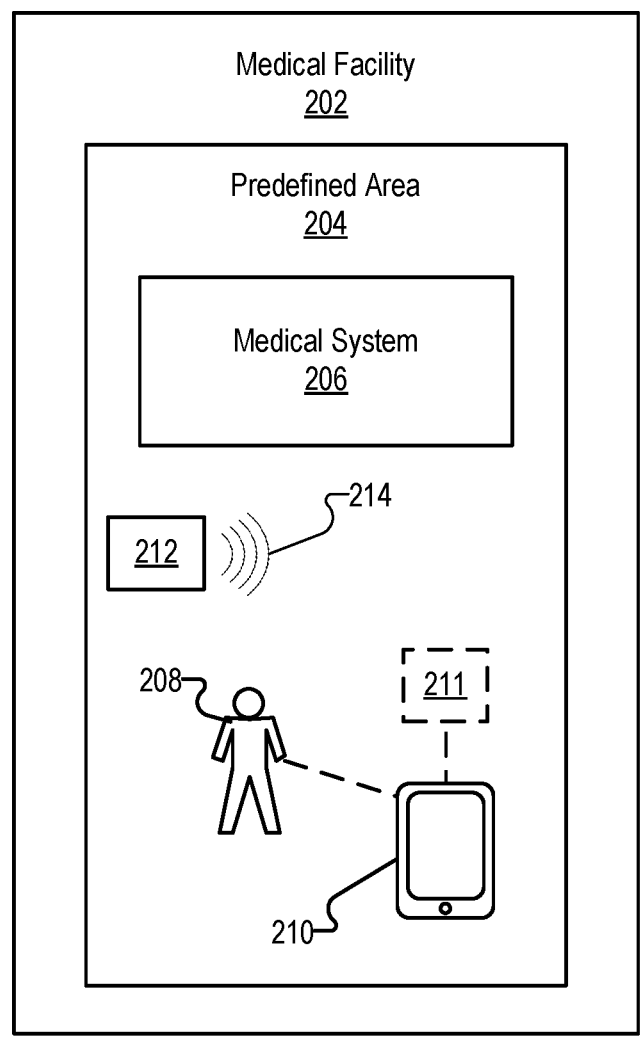
FIGS. 2-6 illustrate exemplary configurations of a medical facility including one or more beacon generators located within a predefined area according to principles described herein.

In some examples a medical system (e.g., surgical system 100) may be located within a medical facility that uses one or more beacons to manage a user's access, by way of an application executed by a user device, to application features associated with a medical session ("medical session features"). FIG. 2 illustrates an exemplary configuration 200 of a medical facility 202. As shown, medical facility 202 includes a predefined area 204 and a medical system 206 located within predefined area 204. Medical facility 202 may be, for example, a hospital, a unit within a hospital (e.g., an emergency room, a trauma center, a maternity unit, an intensive care unit, etc.), a surgical facility, a deployable field hospital, a medical clinic, a doctor's office, a dentist's office, a nursing home, a hospice facility, a rehab facility, an assisted living facility, or any other similar facility. Predefined area 204 is a particular area (e.g., a particular room) within medical facility 202 in which medical system 206 is located and/or used to perform one or more tasks or operations with respect to a patient. For example, predefined area 204 may be an operating room, a recovery room, a consulting room, a patient room, an examination room, an equipment room, or any other suitable room or location. In some examples predefined area 204 is defined by and/or separated from other areas of medical facility 202 (e.g., from an adjoining operating room, from a hallway, from an equipment room, etc.) by one or more physical barriers (e.g., walls, windows, doors, curtains, etc.).

Medical system 206 may be any type of medical system that may be used to monitor, measure, diagnose, treat, and/or assist a patient located within medical facility 202. For example, medical system 206 may be a surgical system (e.g., a computer-assisted surgical system, such as surgical system 100), an imaging system (e.g., a computed tomography (CT) scanner, a magnetic resonance imaging (MRI) scanner, an X-ray machine, etc.), a dialysis machine, a heart-lung machine, a monitoring device (e.g., a heartrate monitor, a blood pressure monitor, etc.), a ventilator, a patient bed, and/or any other medical system.

A user 208 (e.g., a surgical team member 110) located within medical facility 202 may interact with user device 210 to perform various operations and tasks associated with a medical session. User device 210 may be any device capable of presenting information to a user, whether in visual, audio, or haptic format, and/or receiving user input from user 208. For example, user device 210 may be implemented by a mobile device (e.g., a mobile phone, a handheld device, a tablet computing device, a laptop computer, a personal computer, etc.), an audio device (e.g., a speaker, earphones, etc.), a wearable device (e.g., a smartwatch device, an activity tracker, a head-mounted display device, a virtual or augmented reality device, etc.), and/or a display device (e.g., a television, a projector, a monitor, a touch screen display device, etc.).

User device 210 may execute an application 211 that provides user 208 with access to one or more medical session features (e.g., display features, control features, information features, and communication features) associated with a medical session performed, at least in part, in predefined area 204 and/or with medical system 206. Application 211 may be any type of application as may suit a particular implementation. For example, application 211 may be a standalone application locally installed on user device 210 (e.g., a "thick client application"). Alternatively, application 211 may be a client-side application (e.g., a "thin client application" such as a mobile application) locally installed on user device 210 and communicatively coupled with a server-side application installed on a remote computing device (e.g., a remote server communicatively connected to user device 210 by way of a network). As another example, application 211 may be a web application accessible through a browser application installed on user device 210. Regardless of the architecture of application 211, application 211 executed by user device 210 may communicate (e.g., directly or indirectly by way of a remote computing system) with one or more remote computing systems associated with a medical session to provide medical session features.

For example, application 211 may be communicatively connected with a medical facility management system (not shown) maintained by or associated with medical facility 202 to provide user 208 with access to view and/or edit information generated and/or maintained by medical facility 202 ("medical facility information"). Such medical facility information may include, for example, information about the medical facility (e.g., a map of the medical facility, operating hours of the medical facility, a listing of services provided at the medical facility, etc.), patient information (e.g., patient charts, patient medication information, patient contact information, insurance information, etc.), medical personnel information (e.g., a list of service providers, a list of currently assigned surgical teams, etc.), medical session information (e.g., a list of surgical team members assigned to a particular surgical session, a location of a particular medical session, locations within the medical facility of medical personnel, a type of medical procedure being performed on a particular patient, etc.), medical system information (e.g., a list of available medical systems and equipment, availability of particular medical systems, etc.), and/or any other information. Accordingly, user 208 may interact with user device 210 by way of application 211 to view a patient chart, input information into a patient chart (e.g., dosage information), schedule a medical procedure, schedule use of a particular medical system, schedule a particular surgical team for a particular surgical session, schedule performance of a particular task, view a tutorial video (e.g., for use of a particular medical system), update user profile information, and/or perform any other operation.

In additional or alternative examples user device 210 may be communicatively paired with medical system 206 whereby the medical session features provided by application 211 may provide include medical system interaction features associated medical system 206. For instance, application 211 may provide user 208 with access to interact with (e.g., view, download, edit, annotate, control, etc.) content (e.g., visual content and/or audio content) generated by medical system 206, such as an endoscopic video feed generated by surgical system 100, an ultrasound image, an MRI image, a CT scan, an x-ray image, etc. Additionally or alternatively, application 211 may enable user 208 to interact with medical system 206. For instance, application 211 may provide a graphical user interface by which a user may configure settings of medical system 206 and/or control operation of medical system 206 (e.g., control operation of manipulator arms 112 and/or surgical instruments attached to manipulator arms 112).

Medical session features may also enable user 208 to view and/or edit information associated with a particular medical session performed with medical system 206 (e.g., patient information, medical session information, medical notes, etc.), and/or communicate with other users by way of additional user devices that are communicatively paired with medical system 206.

As will be explained below in more detail, application 211 includes a graphical user interface that may be displayed on a display screen of user device 210. The graphical user interface may include various screens, menus, selectable options, windows, backend functionality (e.g., gesture control), and other elements that provide the user with access to the features associated with the medical session.

Beacon generator 212 is located within predefined area 204 and configured to generate and emit a beacon 214. Beacon 214 may be used to manage access to medical session features of application 211. Beacon 214 may also convey contextual information to user device 210 and/or facilitate communicative pairing of user device 210 with medical system 206. Beacon 214 may comprise any suitable push signal, or combination of push signals, that may be detected by user device 210. For example, beacon 214 may include ultrasonic signals, electromagnetic signals (e.g., infrared, radio-frequency identification (RFID), etc.), wireless data signals (e.g., Bluetooth, near-field communication, Wi-Fi, etc.), and the like. Additionally, beacon 214 may be emitted at any suitable timing, such as continuous, intermittent, periodic, random, in response to the occurrence of certain events (e.g., manual activation of a button on beacon generator 212), etc.

In examples in which beacon 214 comprises ultrasonic signals, the ultrasonic signals may have any frequency above the human audible hearing range (e.g., above about 18 kHz). In some examples the ultrasonic signals have a frequency greater than about 20 kHz. User device 210 may be configured to detect (e.g., via a microphone) signals in beacon 214 when user device 210 is in proximity to beacon generator 212. For example, ultrasonic beacons may be configured to not transmit through solid barriers (e.g., walls) and/or be confined to predefined area 204. Accordingly, user device 210 may be configured to detect ultrasonic signals in beacon 214 only when user device 210 is located within the same predefined area (e.g., operating room) as beacon generator 212. In this way access to medical session features may be easily managed based on proximity of user device 210 to predefined area 204 and/or medical system 206.

In some examples beacon 214 is configured to include information (e.g., contextual information and/or identification information). For example, beacon generator 212 (e.g., an ultrasonic transducer) may encode the information in an ultrasonic beacon by modulating one or more of the amplitude, frequency, and waveform of ultrasonic signals (e.g., based on binary phase-shift keying (BPSK), quadrature phase-shift keying (QPSK), quadrature amplitude modulation (QAM), and orthogonal frequency division multiplexing modulation (OFDM) methods), by using an audio QR code format, by multi-frequency bit-coding, and the like.

In some examples the information associates, or may be used to associate, beacon 214 with medical system 206. For example, beacon 214 may include a location identifier that identifies the predefined area (i.e., predefined area 204) in which beacon 214 (or beacon generator 212) is located. The location identifier may be, for example, a unique identification ("ID") number (e.g., a room number) assigned to or otherwise representative of predefined area 204. As another example, beacon 214 may include a medical system identifier (e.g., a surgical system identifier) that identifies the medical system (i.e., medical system 206) with which beacon 214 is associated. The medical system identifier may be a unique medical system ID assigned to or otherwise representative of medical system 206. As yet another example, beacon 214 may include a beacon generator identifier that identifies the particular beacon generator (i.e., beacon generator 212) that emits beacon 214. The beacon generator identifier may be a beacon generator ID assigned to or otherwise representative of beacon generator 212. As a further example, beacon 214 may include a medical session identifier that identifies a particular medical session with which beacon 214 is associated. The medical session identifier may be a medical session ID assigned to or otherwise representative of a particular medical session (e.g., a patient ID, medical team personnel IDs, a surgeon ID, a room ID, a surgical session ID, a medical procedure type ID (e.g., for a hernia repair surgery, a hysterectomy, etc.) etc.). It will be recognized that the foregoing information that may be included in beacon 214 is merely illustrative and not limiting, as beacon 214 may include any other suitable information (e.g., a network address, GPS coordinates, etc.).

As shown in FIG. 2, beacon generator 212 is a standalone device separate from medical system 206 (e.g., beacon generator 212 is not physically integrated with or controlled by medical system 206). As a standalone device beacon generator 212 may be fixedly positioned at any suitable location within predefined area 204, such as on a wall or ceiling of predefined area 204. Alternatively, beacon generator 212 may be a movable standalone device that may be moved and positioned as desired within predefined area 204 and/or within medical facility 202.

Figure 3:
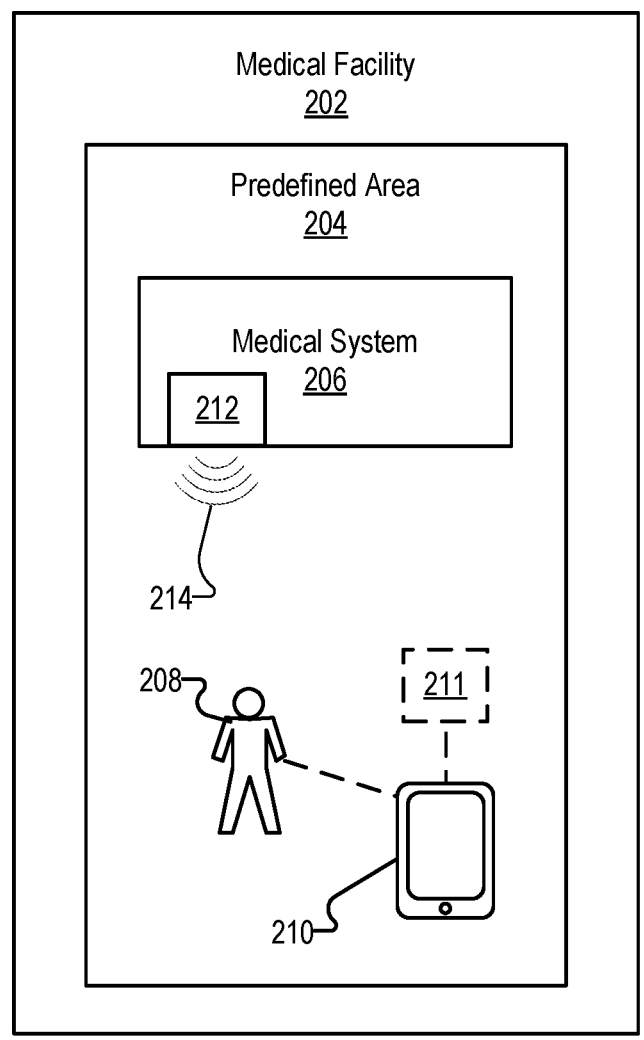

Alternatively to a standalone device separate from medical system 206, beacon generator 212 may be included in medical system 206, as shown in FIG. 3. FIG. 3 illustrates another exemplary configuration 300 of medical facility 202. FIG. 3 is similar to FIG. 2 except that beacon generator 212 is included in medical system 206. Beacon generator 212 may be included in medical system 206 in any suitable way. For example, beacon generator 212 may be physically integrated with medical system 206 (e.g., mounted on a column of manipulating system 102, included in user control system 104, etc.). Thus, if medical system 206 is moved to a different area of medical facility 202, beacon generator 212 also moves to the new area. Additionally or alternatively, beacon generator 212 may be controlled by medical system 206. For example, medical system 206 (e.g., auxiliary system 106 of surgical system 100) may configure beacon 214 to include information and may control the emission of beacon 214 by beacon generator 212.

Figure 4:
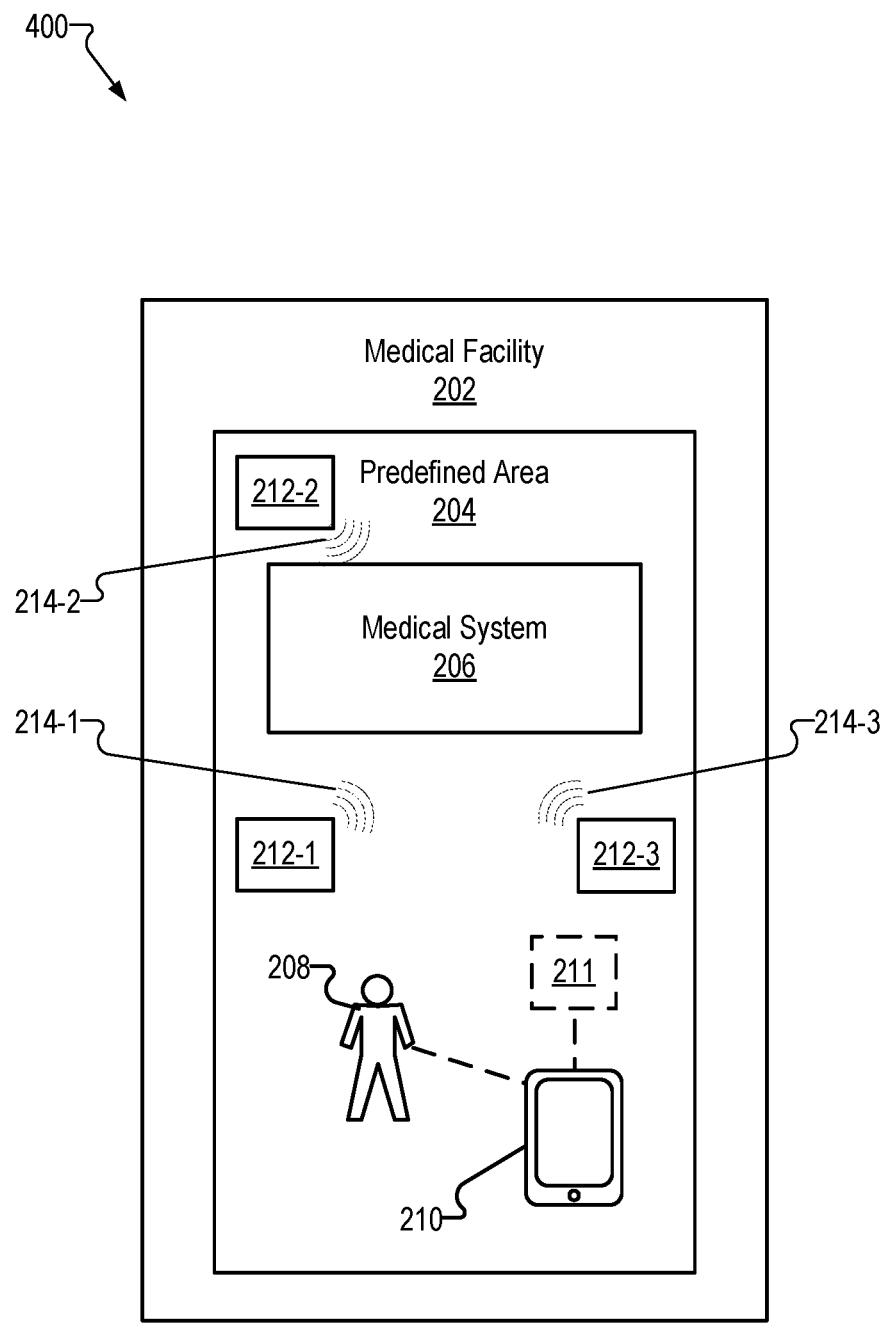

The exemplary configurations 200 and 300 of medical facility 202 described above include a single beacon generator 212 located within predefined area 204. However, multiple beacon generators 212 may be located within predefined area 204, as illustrated in FIG. 4. FIG. 4 illustrates another exemplary configuration 400 of medical facility 202. FIG. 4 is similar to FIG. 2 except that predefined area 204 includes three beacon generators 212 (e.g., beacon generators 212-1 through 212-3) configured to emit ultrasonic beacons 214 (e.g., ultrasonic beacons 214-1 through 214-3). It will be recognized, however, that predefined area 204 may include any other number of beacon generators 212 as may suit a particular implementation.

Ultrasonic beacons 214 may each include information that may be used by a beacon-based application management system to manage access, by a user by way of application 211, to medical session features. In some examples ultrasonic beacons 214 each include the same information (e.g., the same location ID). In additional or alternative examples, each beacon 214 includes unique identification information. For example, beacon 214-1 may include a surgical system identifier, beacon 214-2 may include a location identifier, and beacon 214-3 may include a medical session identifier such as a patient identifier.

Figure 5:
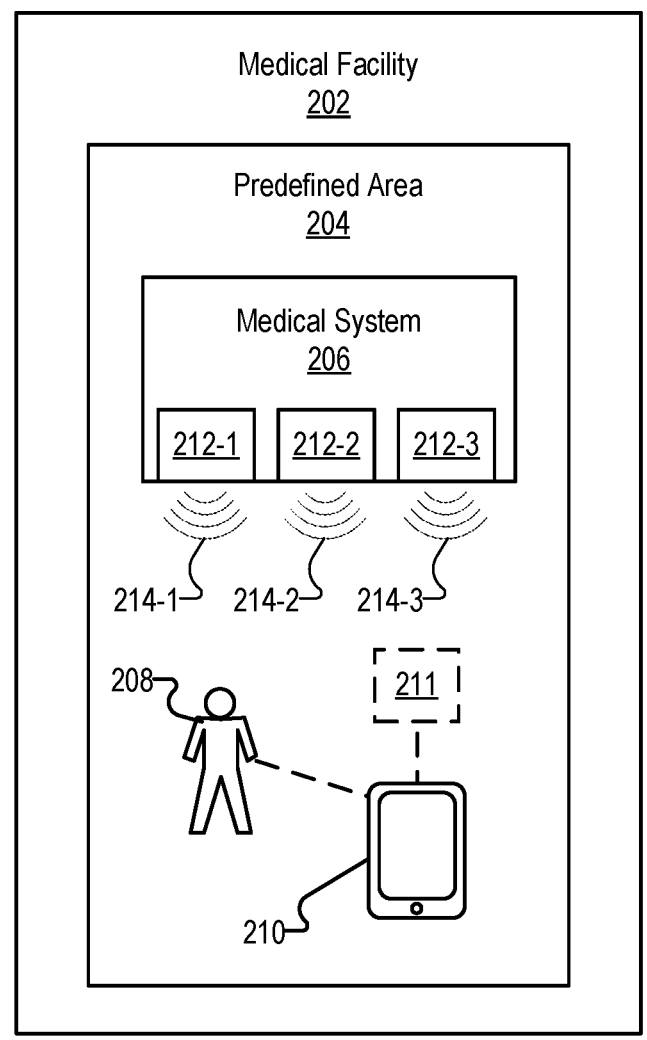

In some examples multiple beacon generators 212 may be included in medical system 206, as shown in FIG. 5. FIG. 5 illustrates another exemplary configuration 500 of medical facility 202. FIG. 5 is similar to FIG. 4 except that beacon generators 212 (e.g., beacon generators 212-1 through 212-3) are included in medical system 206. Beacon generators 212 may be included in medical system 206 in any suitable way. For example, beacon generators 212 may be physically integrated with and/or controlled by medical system 206, as explained above. In some examples each beacon generator 212 is included in a different component of medical system 206. For instance, if medical system 206 is implemented by surgical system 100, beacon generator 212-1 may be included in manipulating system 102, beacon generator 212-2 may be included in user control system 104, and beacon generator 212-3 may be included in auxiliary system 106.

In some examples ultrasonic beacons 214 include the same information (e.g., the same medical system ID). In additional or alternative examples, each beacon 214 includes unique information. For example, when medical system 206 includes multiple components, various components may each include a beacon generator 212 and each beacon 214 may include a unique component identifier (e.g., a component ID) assigned to or otherwise representative of the particular component in which the beacon generator 212 is included. For instance, referring again to the example in which medical system 206 is implemented by surgical system 100, beacon 214-1 may include a unique component ID for manipulating system 102, beacon 214-2 may include a unique component ID for user control system 104, and beacon 214-3 may include a unique component ID for auxiliary system 106.

Figure 6:
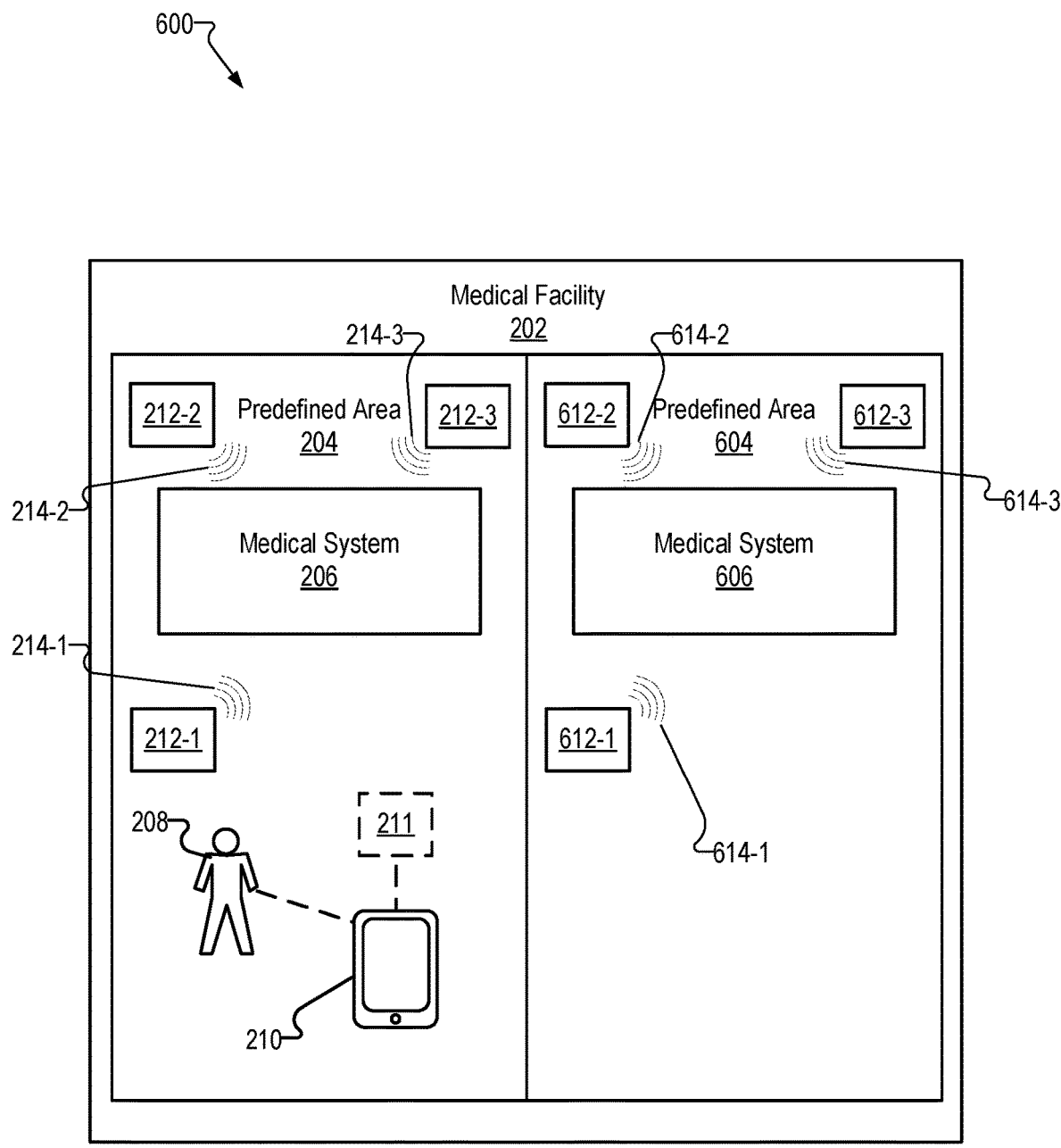

In additional configurations medical facility 202 may also include additional beacon generators (not shown in FIGS. 4 and 5) in areas outside of predefined area 204, as illustrated in FIG. 6. FIG. 6 illustrates another exemplary configuration 600 of medical facility 202. FIG. 6 is similar to FIG. 4 except that medical facility 202 includes an additional predefined area 604 adjoining predefined area 204, additional beacon generators 612 (e.g., beacon generators 612-1 through 612-3) located within predefined area 604 and that emit beacons 614 (e.g., beacons 614-1 through 614-3), and an additional medical system 606 located within predefined area 604. It will be recognized that any of beacon generators 212-1 through 212-3 may alternatively be included in medical system 206, and any of beacon generators 612-1 through 612-3 may alternatively be included in medical system 612, in the manner described above with reference to FIG. 5. Additionally, predefined areas 204 and 604 may each include any other number of beacon generators 212 and 612, respectively, as may suit a particular implementation.

Figure 7:
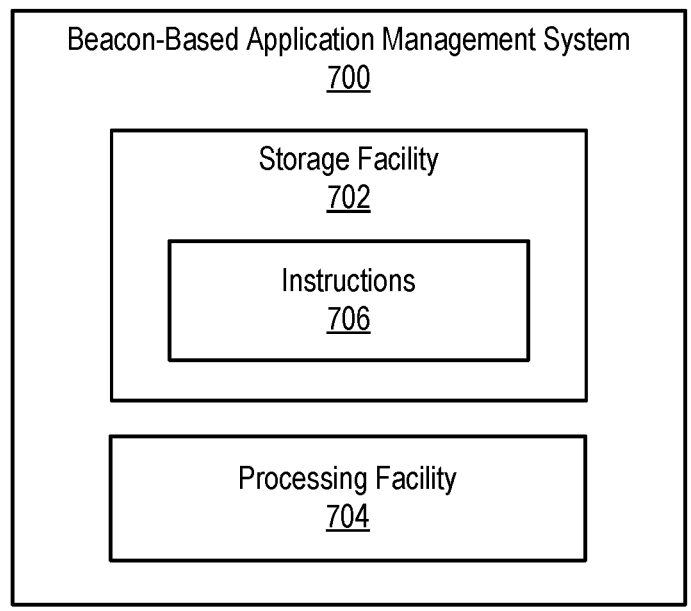
FIG. 7 illustrates an exemplary beacon-based application management system according to principles described herein.

As mentioned, beacons may be used by a beacon-based application management system to manage access, by a user by way of a user device, to medical session features of an application executed by the user device. FIG. 7 illustrates an exemplary beacon-based application management system 700 ("application management system 700") that may be configured to manage access, by a user of a user device, to features of an application executed by the user device and associated with a medical session. Application management system 700 may be included in, implemented by, or connected to any medical systems or other computing systems described herein. For example, application management system 700 may be implemented by a computer-assisted surgical system (e.g., by a computing system included in surgical system 100). As another example, application management system 700 may be implemented by a stand-alone computing system communicatively coupled to a medical system. In some examples application management system 700 may be implemented, in whole or in part, by a user device (e.g., user device 210).

As shown in FIG. 7, application management system 700 includes, without limitation, a storage facility 702 and a processing facility 704 selectively and communicatively coupled to one another. Facilities 702 and 704 may each include or be implemented by hardware and/or software components (e.g., processors, memories, communication interfaces, instructions stored in memory for execution by the processors, etc.). For example, facilities 702 and 704 may be implemented by any component in a medical system. In some examples, facilities 702 and 704 may be distributed between multiple devices and/or multiple locations as may serve a particular implementation.

Storage facility 702 may maintain (e.g., store) executable data used by processing facility 704 to perform any of the operations described herein. For example, storage facility 702 may store instructions 706 that may be executed by processing facility 704 to perform any of the operations described herein. Instructions 706 may be implemented by any suitable application, software, code, and/or other executable data instance. Storage facility 702 may also maintain any data received, generated, managed, used, and/or transmitted by processing facility 704.

Processing facility 704 may be configured to perform (e.g., execute instructions 706 stored in storage facility 702 to perform) various operations associated with managing access, by a user of a user device, to features of an application executed by the user device and associated with a medical session. For example, processing facility 704 may be configured to determine that a user device detects an ultrasonic beacon emitted by a beacon generator located within a predefined area of a medical facility. Processing facility 704 may further be configured to provide, while the user device detects the beacon, a user of the user device with access to a first set of medical session features of an application executed by the user device. Processing facility 704 may further be configured to provide, while the user device does not detect the beacon, the user with access to a second set of medical session features of the application, where the second set of medical session features are different from the first set of medical session features. These and other operations that may be performed by processing facility 704 are described herein. In the description that follows, any references to operations performed by application management system 700 may be understood to be performed by processing facility 704 of application management system 700.

In some exemplary implementations, application management system 700 is implemented entirely by the medical system itself. For example, application management system 700 may be implemented by one or more computing devices included in medical system 206 (e.g., in one or more computing devices included within manipulating system 102, user control system 104, and/or auxiliary system 106 of surgical system 100).

Figure 8:
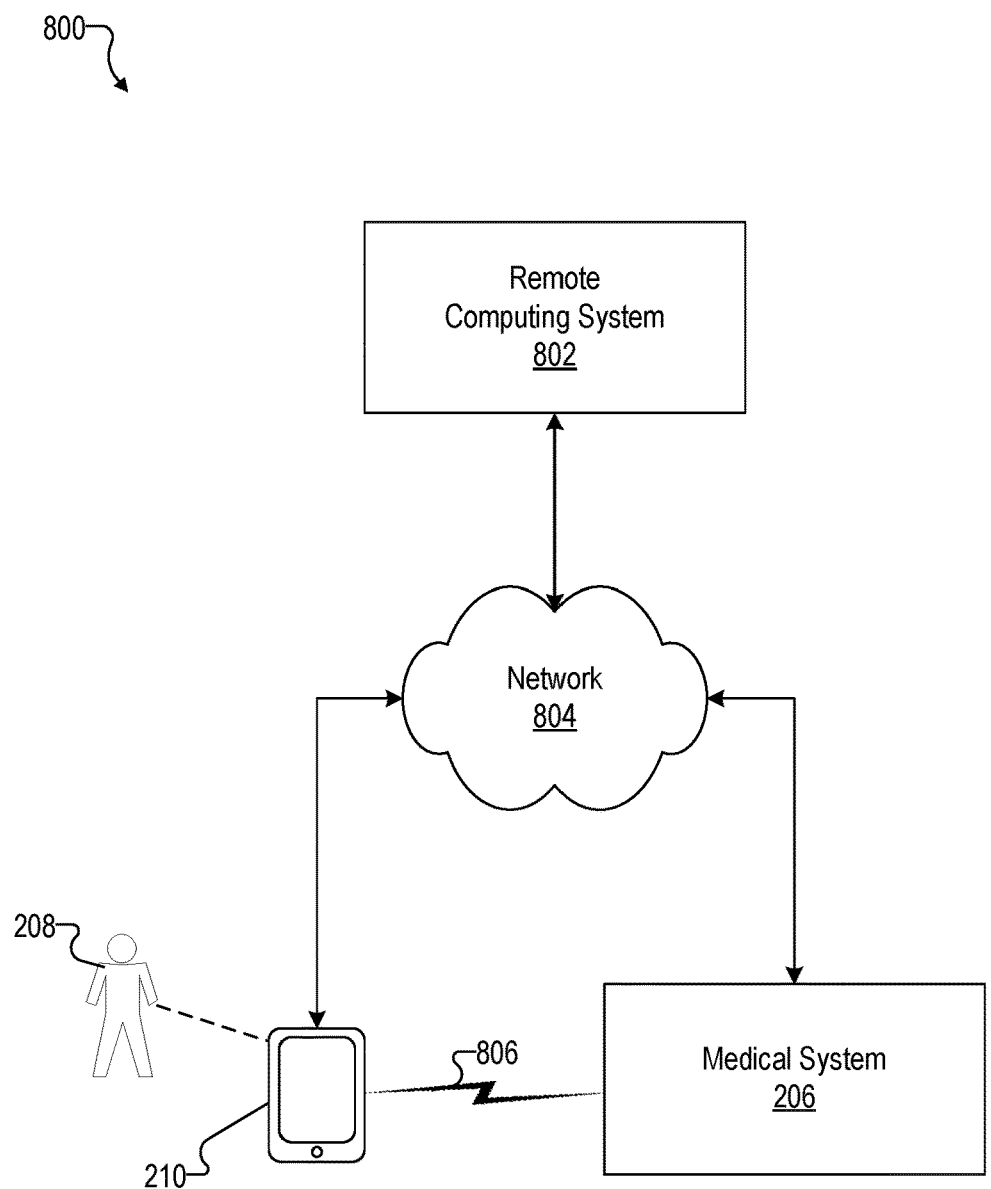
FIG. 8 illustrates an exemplary implementation of the beacon-based application management system of FIG. 7 according to principles described herein.

FIG. 8 illustrates another exemplary implementation 800 of application management system 700. In implementation 800, a remote computing system 802 may be communicatively coupled to medical system 206 by way of a network 804. Remote computing system 802 may include one or more computing devices (e.g., servers) configured to perform any of the operations described herein.

Network 804 may be a local area network, a wireless network (e.g., Wi-Fi), a wide area network, the Internet, a cellular data network, and/or any other suitable network. Data may flow between components connected to network 804 using any communication technologies, devices, media, and protocols as may serve a particular implementation.

As shown, user device 210 may be connected to network 804 and thereby communicate with remote computing system 802. In some examples, user device 210 may also be communicatively paired with medical system 206. When user device 210 is communicatively paired with medical system 206, user device 210 may be configured to exchange data with medical system 206, thereby enabling user 208 to interact, by way of user device 210, with medical system 206.

User device 210 may be communicatively paired with medical system 206 in any suitable way. For example, user device 210 may be communicatively paired with medical system 206 by way of an indirect communication link (e.g., by way of remote computing system 802 and/or network 804). Alternatively, user device 210 may be communicatively paired with medical system 206 by way of a direct (e.g., peer-to-peer, single hop, or ad hoc) communication link 806. The direct communication link may include, for example, a direct wireless connection, such as a Bluetooth connection, a near field communication connection, a Wi-Fi connection, a Wi-Fi Direct connection, a smartphone ad hoc network (SPAN) connection, a mobile device ad hoc network (MANET) connection, etc. In some examples user device 210 may be communicatively paired with medical system 206 only when user device 210 is physically proximate to medical system 206, such as when user device 210 detects a beacon associated with medical system 206 (e.g., beacon 214). It will be recognized, however, that in some examples user device 210 is not communicatively paired with medical system 206.

In some examples remote computing system 802 and/or network 804 are located partly or entirely within a medical facility (e.g., medical facility 202) as part of a medical facility management system (not shown). As explained above, a medical facility management system may include one or more computing systems configured to generate and/or maintain medical facility data associated with the medical facility and its operations, such as data representative of medical systems included in the medical facility and locations of the medical systems, patient information, beacon generator information and locations of the beacon generators, medical session information, medical personnel information, schedule information, and/or any other suitable information.

In some examples, application management system 700 is entirely implemented by remote computing system 802 or user device 210. In alternative examples application management system 700 is distributed across any two or more of remote computing system 802, medical system 206, and user device 210.

Various operations that may be performed by application management system 700 (e.g., by processing facility 704 of application management system 700), and examples of these operations, will now be described. It will be recognized that the operations and examples described herein are merely illustrative of the many different types of operations that may be performed by application management system 700.

Application management system 700 may determine that a user device detects a beacon emitted by a beacon generator located within a predefined area of a medical facility. The user device may detect the beacon in any suitable way. For example, the user device may include a microphone configured to detect ambient sound waves, including an ultrasonic beacon, and process the detected ambient sound waves to generate audio signals representative of the detected ambient sound waves. Additionally or alternatively, the user device may be equipped with an ultrasonic sensor configured to detect the range of ultrasonic beacons emitted in the medical facility. In some examples an application executed by the user device may process the audio signals to filter out audio signals that do not meet a predefined set of criteria (e.g., audio signals that are not in the ultrasonic range, do not fall within a predefined amplitude range, etc.). The microphone (or ultrasonic sensor) may also be set, either automatically by the application or manually by a user, to an "always-on" state. In this way the user device may continually scan for ultrasonic beacons while the user device is moving throughout a medical facility. While in the "always-on" state the user device may sample for ultrasonic beacons at any suitable sampling rate (e.g., 30 Hz). Alternatively to the "always-on" state, the user device may sample for ultrasonic beacons only in response to a user push input (e.g., user input directing the user device to scan for ultrasonic beacons).

In some examples the user device (e.g., the application executed by the user device) analyzes the audio signals to determine whether the audio signals include an ultrasonic beacon. The user device may use any suitable sound processing algorithm to determine whether the audio signals include an ultrasonic beacon. In response to a determination that the audio signals include an ultrasonic beacon, the user device may transmit a notification and/or data representative of the ultrasonic beacon to application management system 700. In response to receipt of the notification and/or the data representative of the ultrasonic beacon, application management system 700 determines that the user device detects an ultrasonic beacon.

In alternative examples, application management system 700 may access the audio signals from the user device and analyze the accessed audio signals to determine whether the audio signals include an ultrasonic beacon. Application management system 700 may use any suitable sound processing algorithm to determine whether the audio signals include an ultrasonic beacon. In some examples the user device may be configured to periodically (e.g., every 5 seconds) transmit the audio signals to application management system 700. If application management system 700 determines that the audio signals include an ultrasonic beacon, application management system 700 determines that the user device detects an ultrasonic beacon.

In response to the determination that the user device detects the beacon and/or while the user device detects the beacon, application management system 700 may provide a user of the user device with access to a first set of medical session features of an application executed by the user device. Application management system 700 may provide access to the first set of medical session features in any suitable way.

In some examples, application management system 700 may select the first set of medical session features from among a plurality of features. The plurality of features may include, for example, default features, user account features, and medical session features. The default features may include, for example, a home screen, a login portal, a settings menu, a contact menu, a help menu, etc. The user account features may be made accessible to a user of the user device upon successful authentication of the user. The user account features may include, for example, access to user account information, login and password settings, user preferences information, user role information, user notes, a user calendar, a list of scheduled tasks or medical sessions for the user, training content tailored for the user, communication features, etc. Medical session features may include, for example, any features associated with a medical session, such as medical system interaction features (e.g., to interact with medical system content, to control operation of the medical system, configure settings of the medical system, etc.), information features (e.g., access to view and/or edit information associated with the medical session), and communication features. In some examples medical session features are made accessible to a user of the user device upon detection, by the user device, of a beacon associated with a medical session. For instance, application management system 700 may select, as the first set of features, all medical session features associated with a particular medical session.

However, some users (e.g., a nurse) may not need access to all medical session features. Therefore, certain medical session features may be made accessible to the user only upon satisfaction of additional criteria, as will now be described.

In some examples the first set of medical session features may be selected from among the plurality of features further based on information included in the detected beacon. As explained above, a beacon may include information such as a location identifier, a medical system identifier, a beacon generator identifier, a medical session identifier, and/or a component identifier. Accordingly, application management system 700 may be configured to identify, in response to a determination that a user device detects a beacon, information included in the beacon.

Application management system 700 may identify information included in the detected beacon in any suitable way. For example, application management system 700 may process and analyze audio signals representative of a detected ultrasonic beacon to identify information included in the detected ultrasonic beacon. For instance, application management system 700 may identify the information included in the ultrasonic beacon by comparing the detected audio signals representative of the ultrasonic beacon with ultrasonic beacon data included in a table of ultrasonic beacon data. The table of ultrasonic beacon data may associate a particular ultrasonic beacon configuration (e.g., a unique combination of amplitude, frequency, waveform, etc.) with a particular instance of information (e.g., a location ID, a medical system ID, a medical session ID, etc.). Application management system 700 may identify the information included in the detected ultrasonic beacon by identifying, in the table of ultrasonic beacon data, a particular instance of information that is associated with an ultrasonic beacon configuration that matches the detected ultrasonic beacon.

In alternative examples the user device (e.g., an application executed by the user device) may identify the information included in the ultrasonic beacon (e.g., in any of the ways described herein) and transmit data representative of the information to application management system 700. Application management system 700 may identify the information included in the ultrasonic beacon based on the data representative of the information transmitted by the user device to application management system 700.

Application management system 700 may provide access to the first set of medical session features of the application based on the information included in the beacon. For example, application management system 700 may provide access to medical session features that are associated with the predefined area, with the medical system, and/or with the medical session identified in the information included in the beacon. This example may be illustrated with reference to FIG. 6. Application management system 700 may determine that information included in beacons 214-1 through 214-3 identifies predefined area 204, medical system 206, and/or a medical session occurring in predefined area 204 and/or performed with medical system 206. Accordingly, application management system 700 may provide user 208 with access, by way of application 211, to an endoscopic video feed generated by medical system 206 (e.g., surgical system 100), control features to interact with medical system 206, patient records for a patient of the medical session occurring in predefined area 204, and/or communication features to communicate with medical personnel located within predefined area 204 and/or performing the medical session.

In some examples the first set of medical session features may be selected from among the plurality of features further based on user data. User data may be representative of user information, such as an identity of a user of the user device, a user role of the user (e.g., surgeon, anesthesiologist, nurse, assistant, technician, orderly, scrub, etc.), and/or a user profile of the user. A user profile may indicate, for example, the user's training level, experience with particular types of medical procedures, preferences, permission levels for medical session features, a listing of assigned tasks, and/or any other suitable information associated with the user.

Application management system 700 may access user data in response to the determination that the user device detects the beacon. Application management system 700 may access the user data in any suitable way. In some examples the user data is accessed from the application executed by the user device (e.g., application 211), which may maintain the user data locally on the user device or remotely on a server device. In some examples the user data is associated with the user device or the application when the user logs into the user device and/or is authenticated by the application. In other examples the user is not logged into or authenticated by the application but may enter the user data (e.g., name or user role) manually. In some examples the user data may be accessed by accessing a user device identification (ID) and identifying user data associated with the user device ID.

Application management system 700 may provide access to the first set of medical session features of the application based on the accessed user data. For example, application management system 700 may determine, based on the accessed user data, that the user is authorized to access a certain set of features of the application. In some examples application management system 700 may determine which features the user is authorized to access based on feature permissions associated with the accessed user data. The feature permissions may be maintained in any suitable location, such as in application management system 700, by the application executed by the user device (e.g., in the user profile), by a medical facility management system, and/or by a medical system.

Application management system 700 may provide access to the set of application features that the user is authorized to access. To illustrate, application management system 700 may determine that user 208 is a surgeon and is authorized to access preoperative medical images (e.g., CT scan images, MRI images, etc.) and communicate with a remote proctor. Accordingly, application management system 700 may provide user 208 with access to view and interact with preoperative medical images. Additionally, application management system 700 may provide user 208 with access to communication features to enable user 208 to communicate with (e.g., call and/or send messages to) the remote proctor.

In some examples the first set of medical session features may be selected from among the plurality of features further based on proximity of the user device to a beacon generator and/or a particular medical system component. In these examples application management system 700 may be configured to determine a proximity of the user device to a particular beacon generator and/or medical system component, and thus determine which beacon generator and/or medical system component is nearest the user device. Application management system 700 may determine the proximity of the user device using any suitable proximity sensing technique, such as based on a signal strength of one or more detected ultrasonic beacon(s), beamforming, and/or triangulation. Additionally or alternatively, application management system 700 may use other techniques not based on ultrasonic beacons, such as Bluetooth, near-field communication, radio frequency identification (RFID), global position satellite systems, and local positioning systems.

Application management system 700 may provide access to the first set of medical session features of the application based on the proximity of the user device to a beacon generator and/or medical system component. To illustrate with reference to FIG. 5, application management system 700 may determine that user device 210 detects beacons 214-1 through 214-3 included in medical system 206 but that user device 210 is nearest to beacon generator 212-1 included in a first component (e.g., user control system 104) of medical system 206. Accordingly, application management system 700 may provide user 208 with access to interact with the first component by way of user device 210 (e.g., adjust ergonomic settings of user control system 104 by way of user device 210).

As mentioned above, while a user device detects a beacon associated with a medical system, application management system 700 may provide a user of the user device with access to a first set of medical session features of the application executed by the user device. Additionally, application management system 700 may provide, while the user device does not detect the beacon, the user with access to a second set of medical session features that is different from the first set of medical session features.

For example, application management system 700 may be configured to determine when the user device no longer detects the beacon, which may occur when the user device is moved out of range of the beacon (e.g., when user device 210 moves out of predefined area 204) or when the beacon generator stops emitting the beacon (such as when a medical session ends). In response to a determination that the user device no longer detects the beacon and/or while the user device does not detect the beacon, application management system 700 may provide the user with access to a second set of medical session features that is different from the first set of medical session features. The second set of medical session features may be different from the first set of medical session features in any suitable way. For example, the second set of features may be limited to a default feature set and/or a user information feature set. In alternative examples, the second set of medical session features may remove or block access to certain features included in the first set of medical session features.

In some examples, the first set of medical session features and the second set of medical session features may both be associated with the same medical session, but the second set of medical session features may include different types of features than the first set of medical session features and/or different access levels or permission levels for similar types of features. To illustrate, while user device 210 is present in predefined area 204 and detects beacon 214, user 208 may be provided, by way of user device 210, with access to view an endoscopic video feed generated by medical system 206 but not annotate the endoscopic video feed. When user device 210 is moved outside of predefined area 204 and no longer detects beacon 214, user 208 may view and annotate the endoscopic video feed.

Application management system 700 may also provide the user with access to a different set of medical session features in response to a determination that the user device detects a second beacon. In some examples the second beacon is detected while the user device no longer detects the first beacon. In other examples, the user device may detect second beacon in addition to the first beacon. In response to the determination that the user device detects a second beacon and/or while the user device detects the second beacon, application management system 700 may provide the user with access to a third set of medical session features that is different from the first set of medical session features and the second set of medical session features.

To illustrate with reference to FIG. 6, user device 210 may detect beacon 214-1 while user device 210 is located within predefined area 204. While user device 210 detects beacon 214-1, application management system 700 may provide user 208 with access, by way of user device 210, to medical session features associated with a first medical session performed in predefined area 204 and/or with medical system 206. When user device 210 is moved to predefined area 604, user device 210 may no longer detect beacon 214-1 but may instead detect beacon 614-1. Accordingly, while user device 210 detects beacon 614-1, application management system 700 may provide user 208 with access, by way of user device 210, to medical session features associated with a second medical session performed in predefined area 604 and/or with medical system 606.

Another example is illustrated with reference to FIG. 5. User device 210 may detect beacon 214-1 while user device 210 is located within predefined area 204. While user device 210 detects beacon 214-1 emitted by a first component included in medical system 206 (e.g., manipulating system 102 of surgical system 100), application management system 700 may provide user 208 with access, by way of user device 210, to medical session features associated with the first component included in medical system 206. As user device 210 is moved farther into predefined area 204, user device 210 may detect beacon 214-2 emitted from a second component (e.g., user control system 104 of surgical system 100) included in medical system 206 in addition to beacon 214-1. Accordingly, application management system 700 may provide user 208 with access, by way of user device 210, to medical session features associated with both the first and second components included in medical system 206.

In some examples, application management system 700 may provide the user with access to a different set of medical session features when the beacon is updated to include new information (e.g., a new location ID, a new medical system ID, a new medical session ID, etc.). Application management system 700 may be configured to determine that the beacon has been updated to include new information and may identify the new information included in the beacon. The new information may be included in the beacon either in addition to or in place of the original information included in the beacon. In response to the determination that the beacon has been updated to include new information and while the user device detects the beacon, application management system 700 may provide, based on the new information included in the beacon, the user with access to a third set of medical session features of the application that is different from the first set of medical session features and the second set of medical session features. In this way application management system 700 may use the beacon to dynamically update the features provided to the user by way of the user device even though the user device has not changed locations.

To illustrate, beacon 214 may include a medical session ID unique to a first medical session performed in predefined area 204. Accordingly, user 208 may be given access to view and edit patient records for a patient of the first medical session. When the first medical session ends and a second medical session begins in predefined area 204, beacon 214 may be updated to include a second medical session ID unique to the second medical session. Accordingly, when user device 210 detects the second medical session ID, application management system 700 may provide user 208 with access, by way of user device 210, to patient records for a patient of the second medical session but may terminate the access to patient records for the patient of the first medical session.

In some examples, the feature permissions for user 208 may also be different for the second medical session than for the first medical session even though the user 208 may not change. For instance, the first medical session may include a surgical procedure that user 208 is performing for the first time. Accordingly, while user device 210 detects beacon 214 during the first medical session, application management system 700 may provide user 208 with access to training videos and tutorials for the surgical procedure, but application management system 700 does not provide user 208 with access to interact with medical system 206. On the other hand, the second medical session may include a different surgical procedure that user 208 has performed many times. Accordingly, while user device 210 detects beacon 214 during the second medical session, application management system 700 may provide user 208 with access to interact with medical system 206 but may not provide access to training videos or tutorials for the second surgical procedure.

Application management system 700 may also provide the user with access to a different set of medical session features when the user data associated with the user device changes. The user data may change, for example, when a user logged in to the user device and/or the application changes (e.g., when a nurse's shift ends and a new nurse logs into the application on the user device), when a role assigned to a user of the user device changes (e.g., from head nurse to assistant nurse), or when user profile information changes (e.g., when a user profile is updated to indicate the user's proficiency with a particular medical system or a particular medical procedure).

Application management system 700 may be configured to determine when the user data has been updated to include new user data. In some examples application management system 700 may be configured to access user data at regular intervals (e.g., in response to each determination that the user device detects a beacon). Alternatively, application management system 700 may receive push notifications (e.g., from the user device, from the application executed by the user device, etc.) of changes to user data.

In response to the determination that the user data has been updated to include new user data and while the user device detects the beacon, application management system 700 may provide, based on the new user data, the new user with access to a third set of medical session features of the application that is different from the first set of medical session features. For example, application management system 700 may determine, based on the new user data, that the new user is authorized to access a third set of medical session features of the application. Application management system 700 may then provide access to the third set of medical session features that the new user is authorized to access.

To illustrate, application management system 700 may determine, based on user data, that user 208 is a particular nurse and has specific assignments to perform certain tasks associated with the medical session (e.g., perform operative tasks). Accordingly, application management system 700 may provide user 208 with access, by way of an application executed by user device 210, to a set of features associated with the nurse's assigned tasks (e.g., medical session images and video content, tutorials, patient information, surgeon's instructions, etc.). When the nurse completes the assigned tasks another nurse (e.g., a postoperative nurse) may log into the application on the same user device. Application management system 700 may determine, based on user data, that user 208 is now a new nurse that has specific assignments to perform certain other tasks associated with the medical session (e.g., perform postoperative tasks). Accordingly, application management system 700 may provide user 208 with access, by way of the application executed by user device 210, to a different set of features associated with the new nurse's assigned tasks (e.g., patient information, recovery care instructions, recovery room information, checkup schedules, etc.).

In the foregoing embodiments, application management system 700 may provide, while a user device detects a beacon associated with a medical system, a user of the user device with access to a first set of medical session features of an application executed by the user device, and provide, while the user device does not detect the beacon, the user with access to a second set of medical session features of the application. Application management system 700 may also provide the user with access to a third set of medical session features in response to a change in the information included in the detected beacon and/or a change in the user data. Application management system 700 may provide the user with access to the first set of medical session features, the second set of medical session features, and the third set of medical session features in any suitable way.

In some examples application management system 700 directs the user device and/or the application executed by the user device to populate the graphical user interface with only those features to which access will be provided. Additionally or alternatively, application management system 700 may direct the user device and/or the application to present all features but block or "freeze" features (e.g., menu items, selectable options, etc.) to which access will not be provided. For example, application management system 700 may provide access to the second set of medical session features by removing or blocking access to certain features included in the first set of medical session features and/or by adding certain other features not included in the first set of medical session features. In some examples application management system 700 may, in addition to providing access to the second set of medical session features or the third set of medical session features, terminate access to all features included in the first set of medical session features and/or the second set of medical session features.

Figure 9:
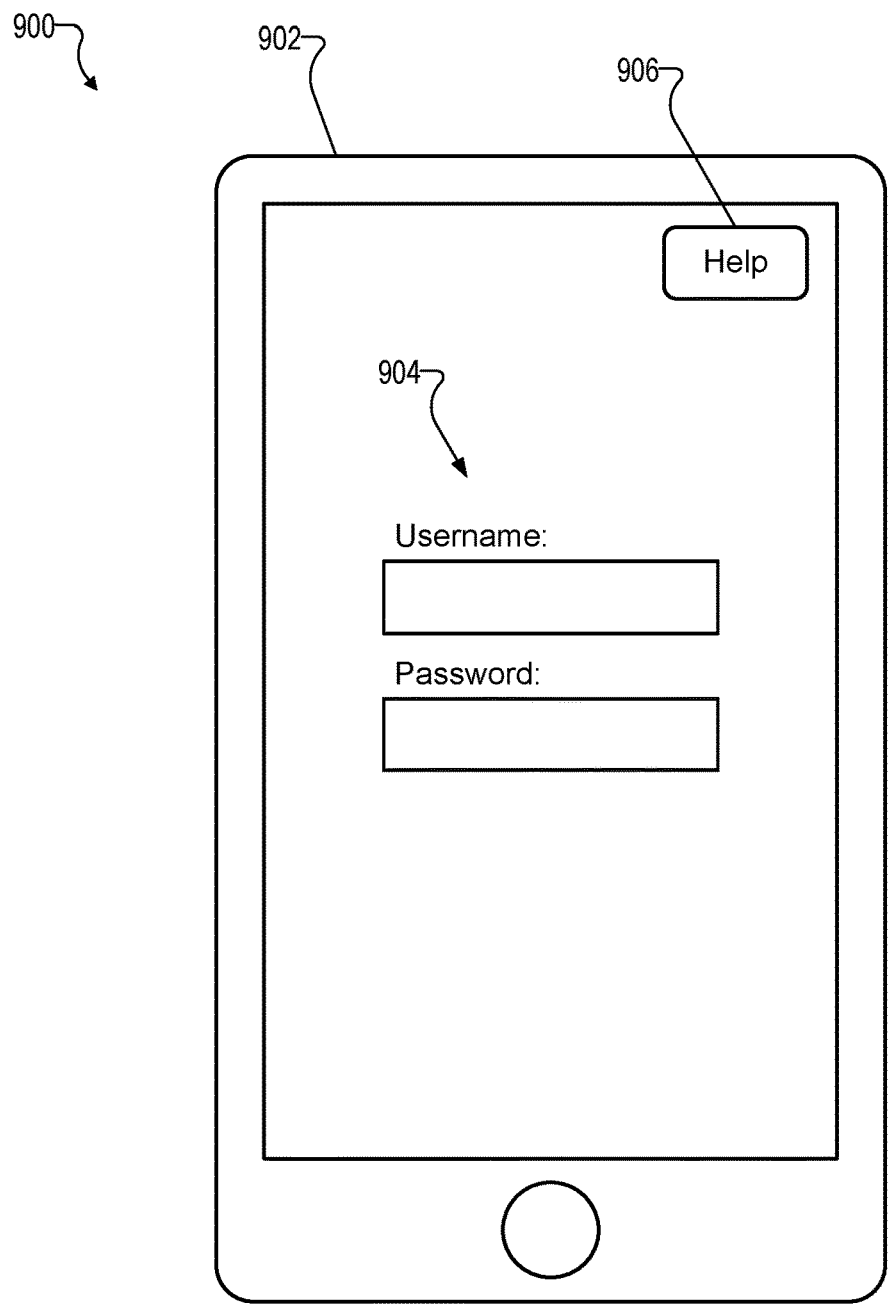
FIGS. 9-13 illustrate exemplary rendered versions of graphical user interface screens of a graphical user interface provided by an application executed by a user device according to principles described herein.

Examples of beacon-based rendering a graphical user interface ("GUI") of an application executed by a user device will now be described with reference to FIGS. 9-13. FIGS. 9-13 show exemplary rendered versions of GUI screens of a graphical user interface provided by an application (e.g., application 211) executed by a user device 902 (e.g., user device 210). FIG. 9 shows an exemplary GUI screen 900 rendered by user device 902 while user device 902 does not detect a beacon. As shown, GUI screen 900 includes a set of default features including a login portal 904 and a selectable option 906 to access a "Help" menu.

Figure 10:
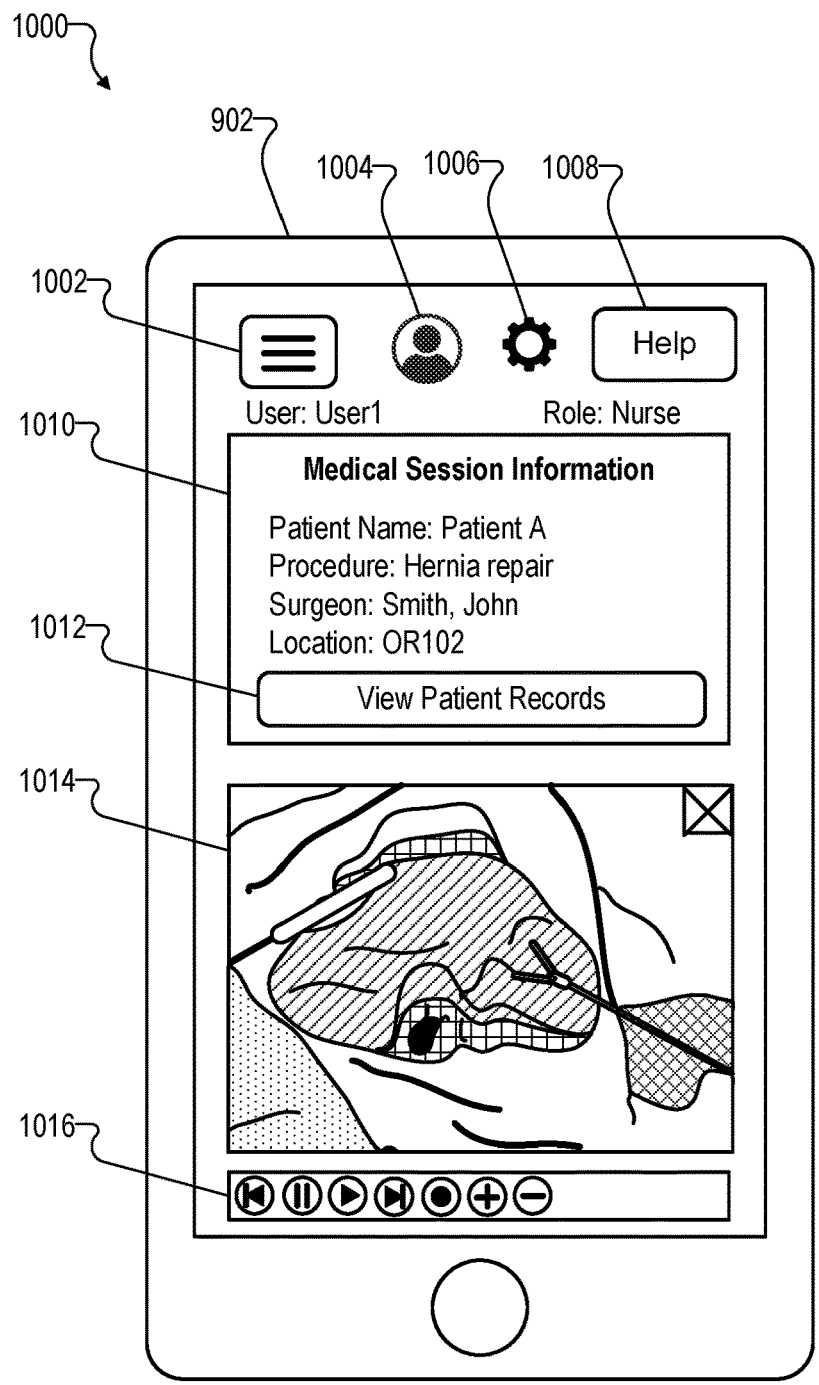

FIG. 10 shows an exemplary GUI screen 1000 rendered by user device 902 in response to a determination that user device 902 detects a beacon. A user may interact with GUI screen 1000 to select one or more options represented in GUI screen 1000 in order to access one or more features associated with a medical session. As shown, GUI screen 1000 includes a main menu option 1002, a user account option 1004, a settings option 1006, and a help option 1008. GUI screen 1000 further includes a window 1010 configured to provide information associated with a medical session, and an option 1012 to view patient records for the patient of the medical session. In some examples the medical session information presented in window 1010 is selected based on information included in the detected beacon.

GUI screen 1000 further includes a media player window 1014 in which images or video (e.g., an endoscopic video feed) are presented. GUI screen 1000 also includes a video playback control menu 1016 by which the user may control the presentation of images or video in media player window 1014.

Figure 11:
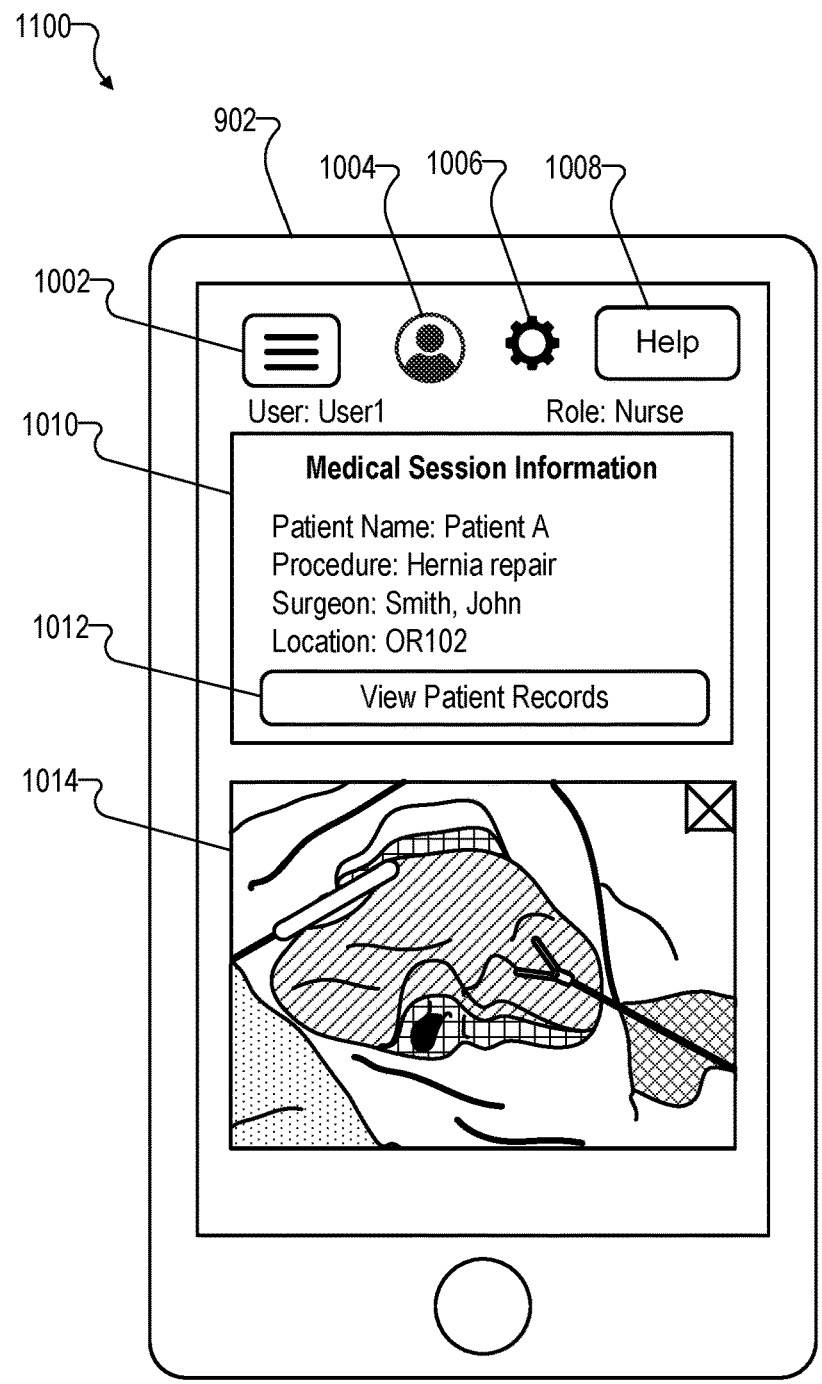

FIG. 11 shows an exemplary GUI screen 1100 rendered by user device 902 in response to a determination that user device 902 no longer detects the beacon. FIG. 11 is the same as FIG. 10 except that set of features accessible through GUI screen 1100 does not include video playback control menu 1016. In some examples GUI screen 1100 may further include a notification or message (not shown) indicating that video control features have been disabled.

Figure 12:
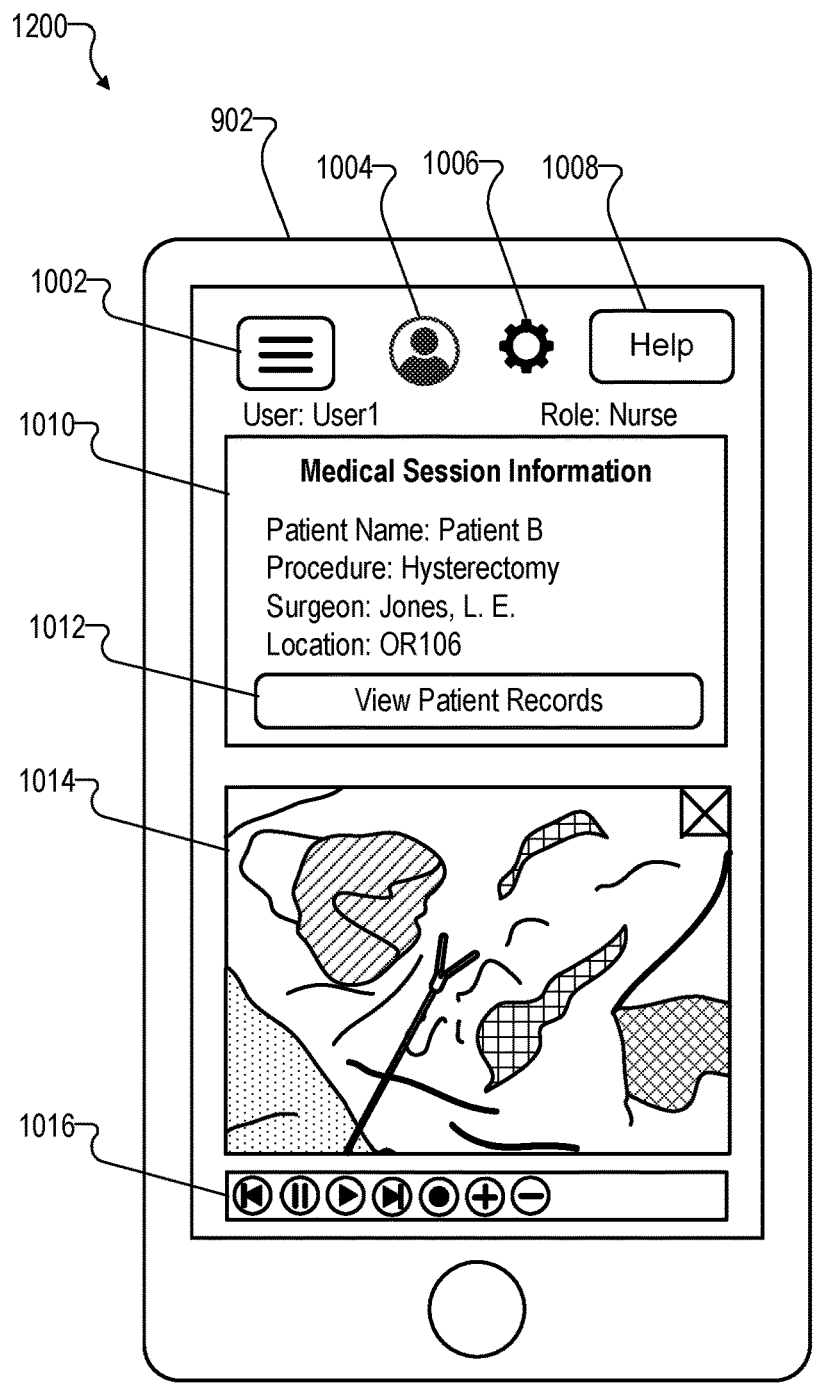

FIG. 12 shows an exemplary GUI screen 1100 rendered by user device 902 in response to a determination that user device 902 detects a second beacon in place of the first beacon. FIG. 12 is the same as FIG. 10 except that the set of features accessible through GUI screen 1200 is associated with a second medical session. Thus, the medical session information presented in window 1010 is associated with the second medical session and the endoscopic video feed presented in window 1014 is generated by a medical system used to perform the second medical session on a second patient.

Figure 13:
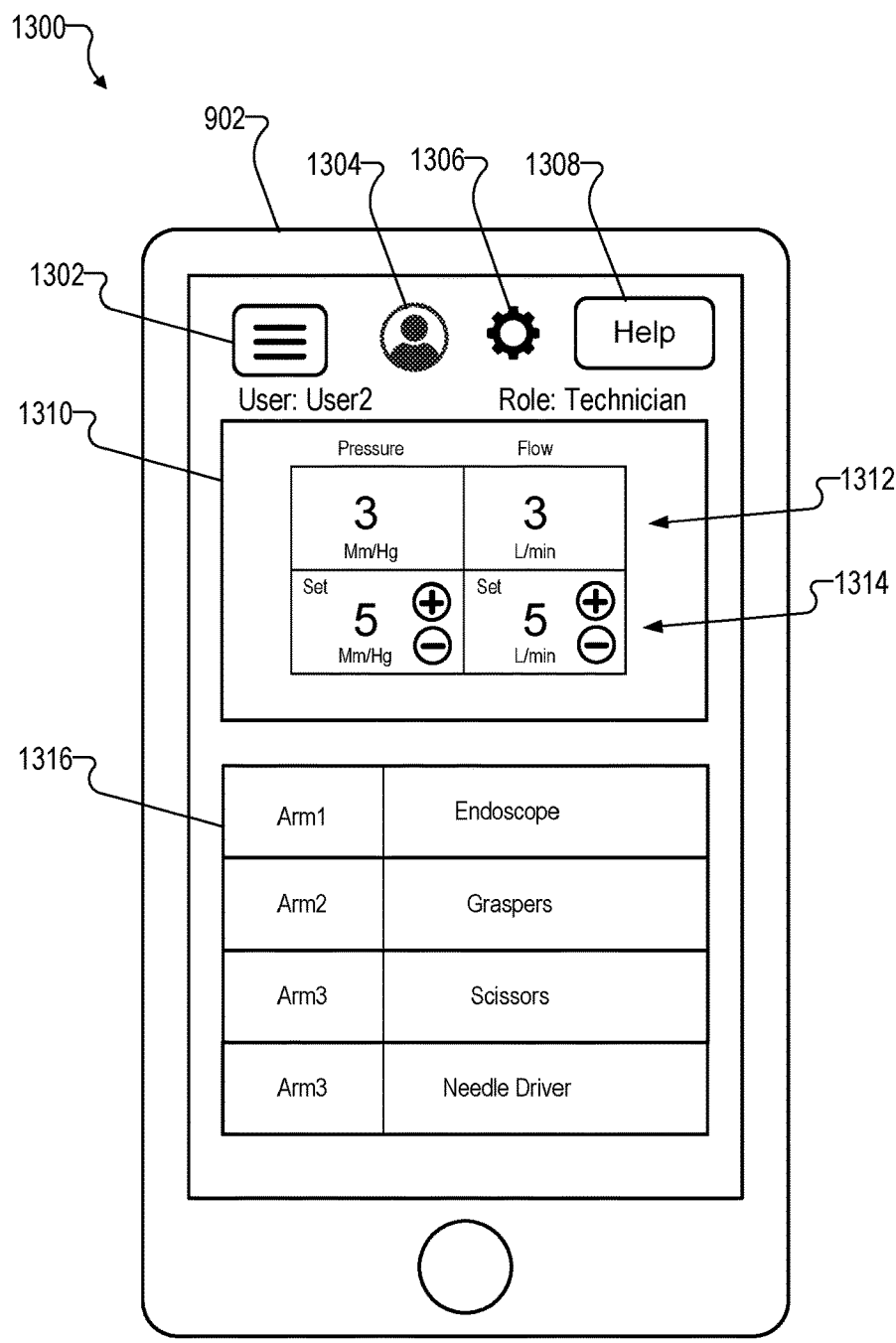

FIG. 13 shows an exemplary GUI screen 1300 rendered by user device 902 in response to a determination that user device 902 no longer detects the beacon and further based on user data indicating that a user role of the user is a technician. As shown, GUI screen 1300 includes a main menu option 1302, a user account option 1304, a settings option 1306, and a help option 1308. Based on the user role, GUI screen 1300 includes a first window 1310 that provides information 1312 about a current state of insufflation and a set of controls 1314 to adjust the insufflation (e.g., adjust the pressure and flowrate of the insufflation gas). GUI screen 1300 also includes a second window 1316 that provides information about surgical instruments coupled to manipulator arms (e.g., manipulator arms 112).

It will be recognized that the GUI screens described above are merely exemplary and not limiting. In some examples a set of features may be provided by way of multiple GUI screens, which may be accessed by various menu options, gestures, and other user input.

Figure 14:
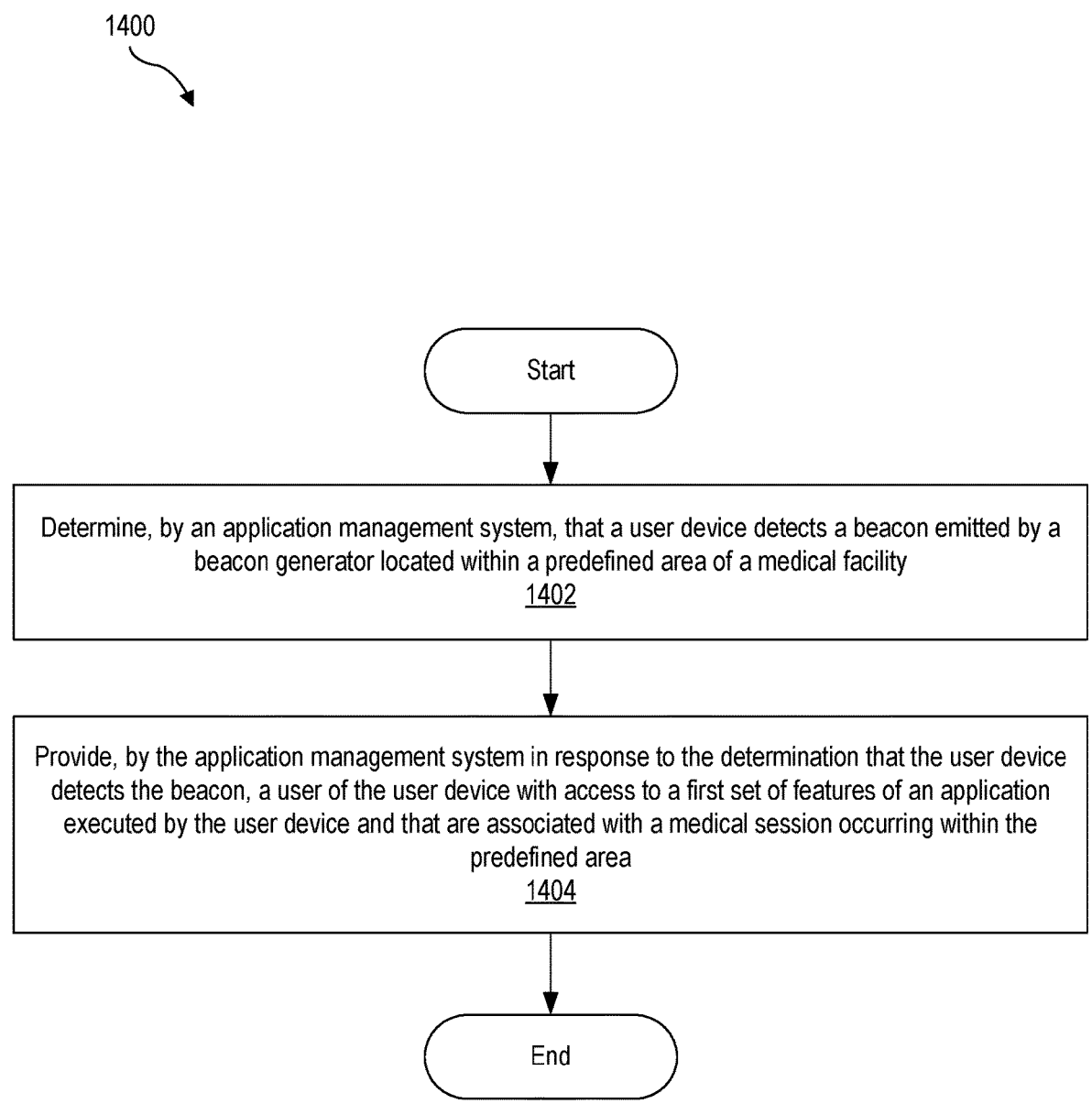
FIG. 14 illustrates an exemplary method according to principles described herein.

FIG. 14 shows an exemplary method 1400. While FIG. 14 illustrates exemplary operations according to one embodiment, other embodiments may omit, add to, reorder, combine, and/or modify any of the steps shown in FIG. 14 One or more of the operations shown in in FIG. 14 may be performed by application management system 700, any components included therein, and/or any implementation thereof.

In operation 1402, a beacon-based application management system provides, while a user device detects a beacon associated with a medical system, a user of the user device with access to a first set of medical session features of an application executed by the user device. Operation 1402 may be performed in any of the ways described herein.

In operation 1404, the beacon-based application management system provides, while the user device does not detect the beacon, the user with access to a second set of medical session features of the application, the second set of medical session features being different from the first set of medical session features. Operation 1404 may be performed in any of the ways described herein.

Figure 15:
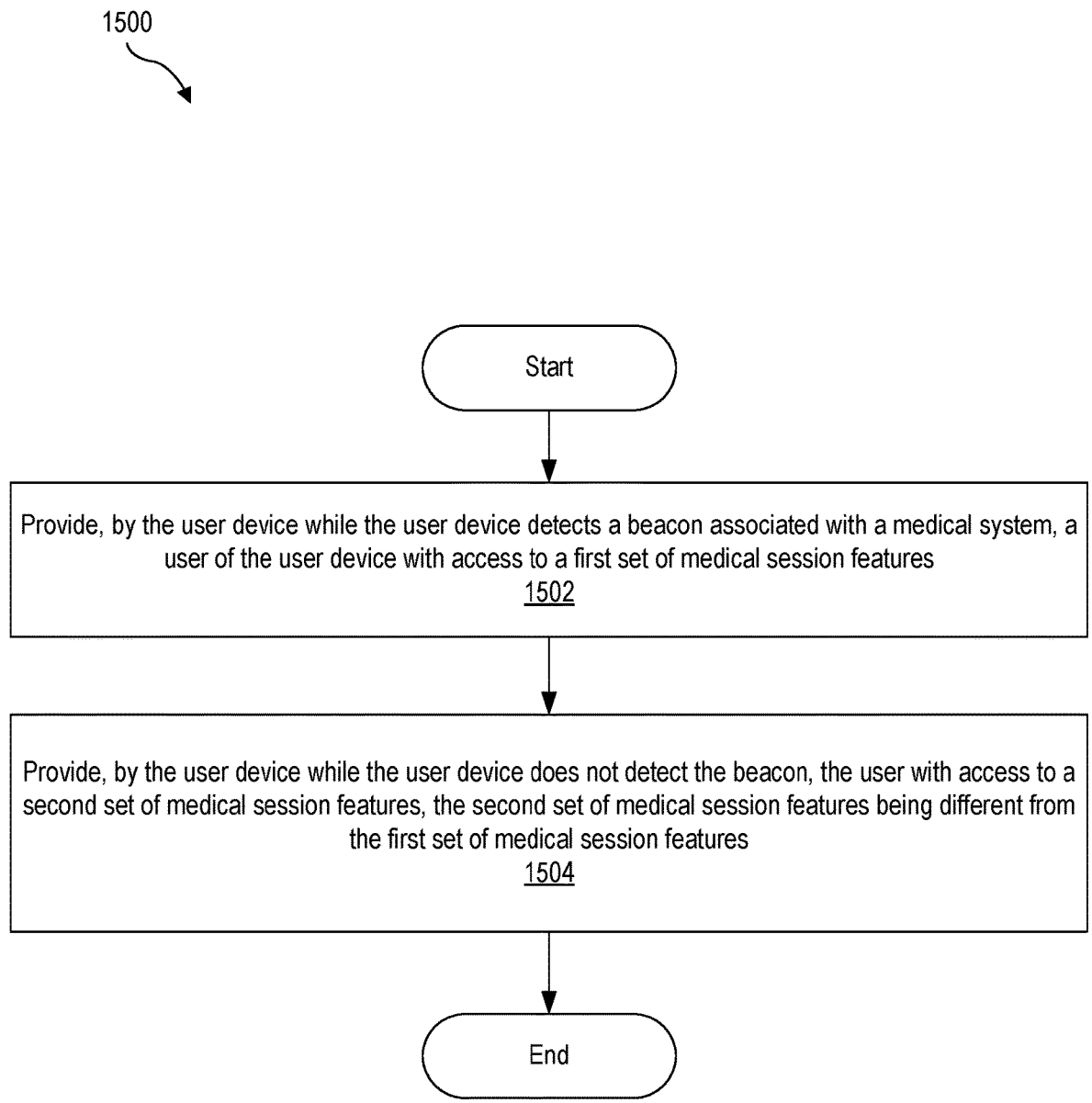
FIG. 15 illustrates another exemplary method according to principles described herein.

FIG. 15 shows another exemplary method 1500. While FIG. 15 illustrates exemplary operations according to one embodiment, other embodiments may omit, add to, reorder, combine, and/or modify any of the steps shown in FIG. 15. One or more of the operations shown in in FIG. 15 may be performed by a user device (e.g., by a processor included in user device 210 or user device 902) and/or by any application executed by the user device (e.g., by application 211) and/or by another computing device.

In operation 1502, a user device provides, while the user device detects a beacon associated with a medical system, a user of the user device with access to a first set of medical session features. Operation 1502 may be performed in any of the ways described herein.

In operation 1504, the user device provides, while the user device does not detect the beacon, the user with access to a second set of medical session features, the second set of medical session features being different from the first set of medical session features. Operation 1504 may be performed in any of the ways described herein.

The foregoing configurations and embodiments have focused on beacon-based systems and methods of managing user access to a set of application features associated with a medical session. However, the present disclosure is not limited to these configurations and embodiments, as various modifications and changes may be made thereto without departing from the scope of the inventive principles described herein. For example, the application management systems described herein may be configured to manage access, by way of a device other than a user device, to medical session features. The device may include, for example, a medical device, a component of a medical system 202 (e.g., manipulating system 102, user control system 104, auxiliary system 106, etc.), an accessory cart, and any other suitable device. In other examples, the application management systems described herein may be configured to manage access, by way of a device other than a user device, to features other than medical session features. Additionally or alternatively, the systems and methods described herein may be used to manage user access to application features in association with other types of facilities and environments, such as recreational facilities (e.g., amusement parks, sports stadiums, parks, etc.), educational facilities (e.g., schools, universities, etc.), shopping centers, business facilities (e.g., offices, research parks, etc.), laboratories, manufacturing facilities, transportation facilities (e.g., airports, train stations, etc.), and/or any other suitable facility or environment.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 16:
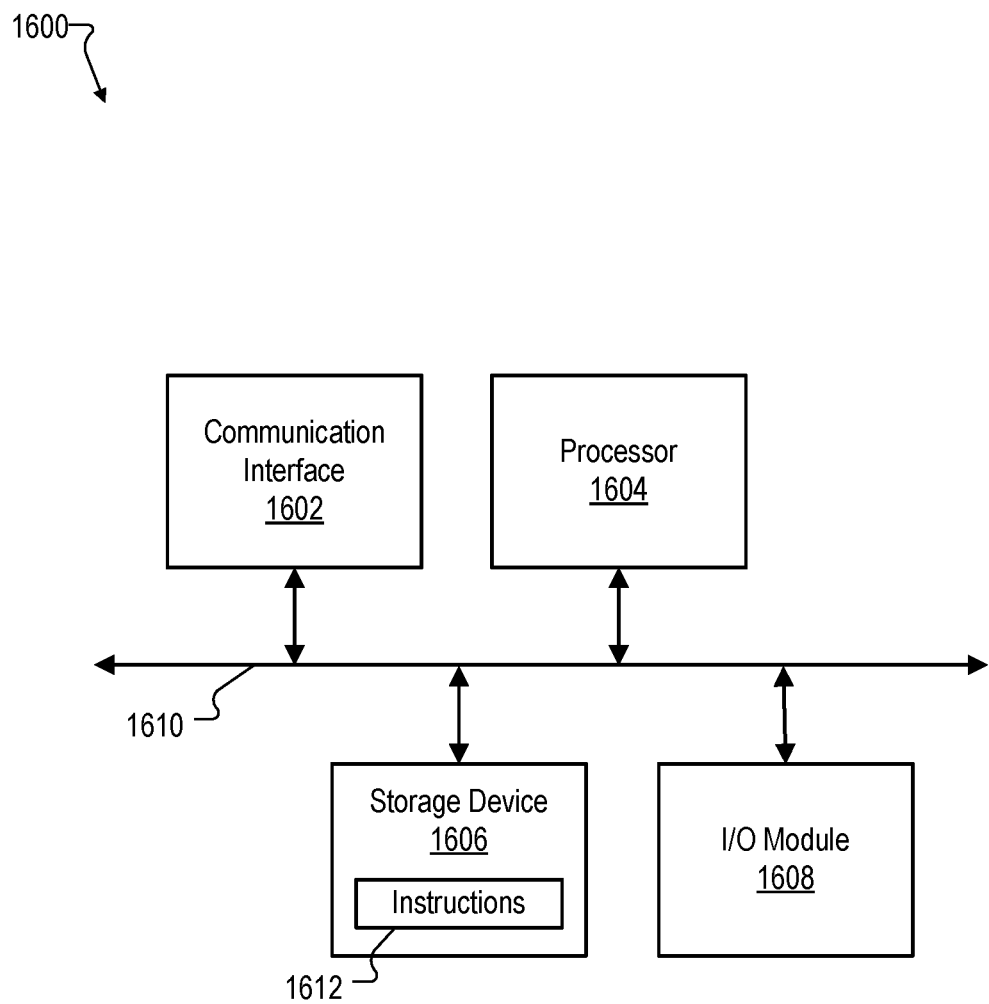
FIG. 16 illustrates an exemplary computing device according to principles described herein.

FIG. 16 illustrates an exemplary computing device 1600 that may be specifically configured to perform one or more of the processes described herein. Any of the systems, units, computing devices, and/or other components described herein may be implemented by computing device 1600, including but not limited to medical system 206, user device 210, medical system 606, application management system 700, remote computing system 802, and user device 902.

As shown in FIG. 16, computing device 1600 may include a communication interface 1602, a processor 1604, a storage device 1606, and an input/output ("I/O") module 1608 communicatively connected one to another via a communication infrastructure 1610. While an exemplary computing device 1600 is shown in FIG. 16, the components illustrated in FIG. 16 are not intended to be limiting. Additional or alternative components may be used in other embodiments. Components of computing device 1600 shown in FIG. 16 will now be described in additional detail.

Communication interface 1602 may be configured to communicate with one or more computing devices. Examples of communication interface 1602 include, without limitation, a wired network interface (such as a network interface card), a wireless network interface (such as a wireless network interface card), a modem, an audio/video connection, and any other suitable interface.

Processor 1604 generally represents any type or form of processing unit capable of processing data and/or interpreting, executing, and/or directing execution of one or more of the instructions, processes, and/or operations described herein. Processor 1604 may perform operations by executing computer-executable instructions 1612 (e.g., an application, software, code, and/or other executable data instance) stored in storage device 1606.

Storage device 1606 may include one or more data storage media, devices, or configurations and may employ any type, form, and combination of data storage media and/or device. For example, storage device 1606 may include, but is not limited to, any combination of the non-volatile media and/or volatile media described herein. Electronic data, including data described herein, may be temporarily and/or permanently stored in storage device 1606. For example, data representative of computer-executable instructions 1612 configured to direct processor 1604 to perform any of the operations described herein may be stored within storage device 1606. In some examples, data may be arranged in one or more databases residing within storage device 1606.

I/O module 1608 may include one or more I/O modules configured to receive user input and provide user output. I/O module 1608 may include any hardware, firmware, software, or combination thereof supportive of input and output capabilities. For example, I/O module 1608 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1608 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1608 is configured to provide graphical data to a display for presentation to a user. The graphical data may be representative of one or more graphical user interfaces and/or any other graphical content as may serve a particular implementation.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a memory storing instructions; and
a processor communicatively coupled to the memory and configured to execute the instructions to:
provide, during a medical session and by way of a graphical user interface while a user device detects one or more wireless or ultrasonic signals associated with a medical system, access to a first set of medical session features of an application executed by the user device, and
provide, by way of the graphical user interface while the user device does not detect the one or more wireless or ultrasonic signals associated with the medical system, access to a second set of medical session features of the application, the second set of medical session features being different from the first set of medical session features,
wherein:
the medical system comprises a computer-assisted surgical system including a manipulating system and a user control system;
the manipulating system includes a manipulator arm configured to couple with a surgical instrument;
the user control system remotely controls at least one of the manipulator arm or the surgical instrument based on user input to perform one or more operations with respect to a subject during the medical session; and
the first set of medical session features comprises a medical system interaction feature configured to allow interaction, by a user of the user device, with the computer-assisted surgical system during the medical session.

2. The system of claim 1, wherein the processor is further configured to execute the instructions to:
identify, while the user device detects the one or more wireless or ultrasonic signals associated with the medical system, information included in the one or more wireless or ultrasonic signals associated with the medical system, and
select the first set of medical session features based on the information included in the one or more wireless or ultrasonic signals associated with the medical system.

3. The system of claim 2, wherein the processor is further configured to execute the instructions to:
determine, while the user device detects the one or more wireless or ultrasonic signals associated with the medical system, that the one or more wireless or ultrasonic signals associated with the medical system has been updated to include new information,
identify the new information included in the one or more wireless or ultrasonic signals associated with the medical system, and
provide, by way of the graphical user interface and based on the new information included in the one or more wireless or ultrasonic signals associated with the medical system, access to a third set of medical session features of the application, the third set of medical session features being different from the first set of medical session features and the second set of medical session features.

4. The system of claim 2, wherein the processor is further configured to execute the instructions to:
determine, while the user device detects the one or more wireless or ultrasonic signals associated with the medical system, that the one or more wireless or ultrasonic signals associated with the medical system has been updated to include new information, and
terminate, in response to the determination that the one or more wireless or ultrasonic signals associated with the medical system has been updated to include new information, the access to the first set of medical session features.

5. The system of claim 1, wherein the processor is further configured to execute the instructions to:
abstain, while the user device does not detect the one or more wireless or ultrasonic signals associated with the medical system, from providing, by way of the graphical user interface, access to the first set of medical session features.

6. The system of claim 1, wherein the processor is further configured to execute the instructions to:
provide, by way of the graphical user interface while the user device detects one or more wireless or ultrasonic signals associated with another medical system, access to a third set of medical session features of the application, the third set of medical session features being different from the first set of medical session features and the second set of medical session features.

7. The system of claim 6, wherein the processor is further configured to execute the instructions to:
abstain, while the user device detects the one or more wireless or ultrasonic signals associated with the another medical system, from providing, by way of the graphical user interface, access to the first set of medical session features.

8. The system of claim 1, wherein:
the medical system interaction feature comprises presentation of an endoscopic video feed provided by the computer-assisted surgical system.

9. The system of claim 1, wherein the medical system interaction feature is configured to allow control, by the user of the user device, of one or more operations or settings of the computer-assisted surgical system during the medical session.

10. A method comprising:
providing, by an application management system during a medical session and by way of a graphical user interface while a user device detects one or more wireless or ultrasonic signals associated with a medical system, access to a first set of medical session features of an application executed by the user device; and
providing, by the application management system and by way of the graphical user interface while the user device does not detect the one or more wireless or ultrasonic signals associated with the medical system, access to a second set of medical session features of the application, the second set of medical session features being different from the first set of medical session features,
wherein:
the medical system comprises a computer-assisted surgical system including a manipulating system and a user control system;
the manipulating system includes a manipulator arm configured to couple with a surgical instrument;
the user control system remotely controls at least one of the manipulator arm or the surgical instrument based on user input to perform one or more operations with respect to a subject during the medical session; and
the first set of medical session features comprises a medical system interaction feature configured to allow interaction, by a user of the user device, with the computer-assisted surgical system during the medical session.

11. The method of claim 10, further comprising:
identifying, by the application management system while the user device detects the one or more wireless or ultrasonic signals associated with the medical system, information included in the one or more wireless or ultrasonic signals associated with the medical system; and
selecting, by the application management system, the first set of medical session features based on the information included in the one or more wireless or ultrasonic signals associated with the medical system.

12. The method of claim 11, further comprising:
determining, by the application management system while the user device detects the one or more wireless or ultrasonic signals associated with the medical system, that the one or more wireless or ultrasonic signals associated with the medical system has been updated to include new information;
identifying, by the application management system, the new information included in the one or more wireless or ultrasonic signals associated with the medical system; and
providing, by the application management system and by way of the graphical user interface based on the new information included in the one or more wireless or ultrasonic signals associated with the medical system, access to a third set of medical session features of the application, the third set of medical session features being different from the first set of medical session features and the second set of medical session features.

13. The method of claim 11, further comprising:
determining, by the application management system while the user device detects the one or more wireless or ultrasonic signals associated with the medical system, that the one or more wireless or ultrasonic signals associated with the medical system has been updated to include new information; and
terminating, by the application management system in response to the determination that the one or more wireless or ultrasonic signals associated with the medical system has been updated to include new information, the access to the first set of medical session features.

14. The method of claim 10, further comprising:
abstaining, by the application management system while the user device does not detect the one or more wireless or ultrasonic signals associated with the medical system, from providing, by way of the graphical user interface, access to the first set of medical session features.

15. The method of claim 10, further comprising:
providing, by the application management system and by way of the graphical user interface while the user device detects one or more wireless or ultrasonic signals associated with another medical system, access to a third set of medical session features of the application, the third set of medical session features being different from the first set of medical session features and the second set of medical session features.

16. The method of claim 15, further comprising:
abstaining, by the application management system while the user device detects the one or more wireless or ultrasonic signals associated with the another medical system, from providing, by way of the graphical user interface, access to the first set of medical session features.

17. The method of claim 10, further comprising:
accessing, by the application management system while the user device detects the one or more wireless or ultrasonic signals associated with the medical system, user data representative of at least one of a user identification of the user of the user device, a user profile of the user, and a user role of the user; and
determining, by the application management system based on the user data, that the user is authorized to access the first set of medical session features,
wherein the providing of the access to the first set of medical session features is based on the determination that the user is authorized to access the first set of medical session features.

18. The method of claim 17, further comprising:
determining, by the application management system while the user device detects the one or more wireless or ultrasonic signals associated with the medical system, that the user data has been updated to new user data representative of at least one of a user identification of a new user of the user device, a user profile of the new user, or a user role of the new user;
determining, by the application management system based on the new user data, that the new user is authorized to access a third set of medical session features of the application; and
providing, by the application management system based on the new user data and while the user device detects the one or more wireless or ultrasonic signals associated with the medical system, the new user with access to the third set of medical session features, the third set of medical session features being different from the first set of medical session features and the second set of medical session features.

19. The method of claim 17, further comprising:

determining, by the application management system while the user device detects the one or more wireless or ultrasonic signals associated with the medical system, that the user data has been updated to new user data representative of at least one of a user identification of a new user of the user device, a user profile of the new user, and a user role of the new user; and terminating, by the application management system in response to the determination that the user data has been updated to new user data, the access to the first set of medical session features.

20. A non-transitory computer-readable medium storing instructions that, when executed, direct at least one processor of a computing device to:

provide, during a medical session and while a user device detects one or more wireless or ultrasonic signals associated with a medical system, a user of the user device with access to a first set of medical session features of an application executed by the user device; and provide, while the user device does not detect the one or more wireless or ultrasonic signals associated with the medical system, the user with access to a second set of medical session features of the application, the second set of medical session features being different from the first set of medical session features, wherein:
- the medical system comprises a computer-assisted surgical system including a manipulating system and a user control system;
- the manipulating system includes a manipulator arm configured to couple with a surgical instrument;
- the user control system remotely controls at least one of the manipulator arm or the surgical instrument based on user input to perform one or more operations with respect to a subject during the medical session; and
- the first set of medical session features comprises a medical system interaction feature configured to allow interaction, by the user of the user device, with the computer-assisted surgical system during the medical session.

* * * * *